United States Patent [19]
Delmotte et al.

[11] Patent Number: 6,074,663
[45] Date of Patent: Jun. 13, 2000

[54] METHOD OF USING CROSS-LINKED FIBRIN MATERIAL

[75] Inventors: Yves Delmotte, Tertre; Genevieve Krack, Gembloux, both of Belgium

[73] Assignee: Baxter International Inc., Deerfield, Ill.

[21] Appl. No.: 08/860,864

[22] PCT Filed: Jan. 16, 1996

[86] PCT No.: PCT/EP96/00160

§ 371 Date: Aug. 28, 1997

§ 102(e) Date: Aug. 28, 1997

[87] PCT Pub. No.: WO96/22115

PCT Pub. Date: Jul. 25, 1996

[30] Foreign Application Priority Data

Jan. 16, 1995 [DE] Germany ............... 195 01 067

[51] Int. Cl.$^7$ .................................. A61F 13/00
[52] U.S. Cl. .............. 424/443; 424/422; 424/423; 424/424; 424/426
[58] Field of Search ............... 424/443, 422, 424/423, 424, 426

[56] References Cited

U.S. PATENT DOCUMENTS

| | | | |
|---|---|---|---|
| 2,533,004 | 12/1950 | Ferry et al. | 260/112 |
| 2,576,006 | 11/1951 | Ferry et al. | 154/88 |
| 3,523,807 | 8/1970 | Gerendas | 106/124 |
| 3,723,244 | 3/1973 | Breillatt | 162/151 |
| 4,016,877 | 4/1977 | Cruz, Jr. et al. | 128/156 |
| 4,066,083 | 1/1978 | Ries | 128/325 |
| 4,116,898 | 9/1978 | Dudley et al. | 260/17.4 |
| 4,148,664 | 4/1979 | Cruz, Jr. | 106/161 |
| 4,225,580 | 9/1980 | Rothman et al. | 424/78 |
| 4,238,480 | 12/1980 | Sawyer | 424/177 |
| 4,442,655 | 4/1984 | Stroetmann | 53/428 |
| 4,505,817 | 3/1985 | Blomback et al. | 210/484 |
| 4,505,822 | 3/1985 | Blomback et al. | 210/635 |
| 4,537,767 | 8/1985 | Rothman et al. | 424/78 |
| 4,548,736 | 10/1985 | Muller | 252/315.1 |
| 4,578,067 | 3/1986 | Cruz, Jr. | 604/368 |
| 4,587,018 | 5/1986 | Blomback et al. | 210/484 |
| 4,600,533 | 7/1986 | Chu | 530/356 |
| 4,606,337 | 8/1986 | Zimmerman | 128/156 |
| 4,621,631 | 11/1986 | Paques et al. | 128/156 |
| 4,631,055 | 12/1986 | Redl et al. | 604/82 |
| 4,640,778 | 2/1987 | Blomback | 210/484 |
| 4,655,980 | 4/1987 | Chu | 264/102 |
| 4,675,361 | 6/1987 | Ward, Jr. | 525/92 |

(List continued on next page.)

FOREIGN PATENT DOCUMENTS

| | | |
|---|---|---|
| 0 068 149 A2 | 1/1983 | European Pat. Off. . |
| 0 085 166 A1 | 8/1983 | European Pat. Off. . |
| 0 166 263 A1 | 1/1986 | European Pat. Off. . |

(List continued on next page.)

OTHER PUBLICATIONS

The Use of Fibrin Paper and Forms in Surgery, May 4, 1916, S.C. Harvey, Boston Medical & Surgical Journal.

Fibrin Clots, Fibrin Films, and Fibrinogen Plastics, Feb. 17, 1944, John D. Ferry and Peter R. Morrison, J. Clin. Invest.

Fibrin Films in Neurosurgery, With Special Reference to Their Use in the Repair of Dural Defects and in the Prevention of Meningocerebral Adhesions, Feb. 17, 1944, Orville T. Bailey and Franc D. Ingraham, J. Clin. Invest.

(List continued on next page.)

Primary Examiner—D. Gabrielle Brouillette
Attorney, Agent, or Firm—Wallenstein & Wagner, Ltd.

[57] ABSTRACT

The self-supporting sheet-like material of cross linked fibrin has a regular pore size. It is used as a bio-mechanical barrier for the treatment of internal traumatic lesions, in particular for the prevention of adhesion formation as a post-operative complication. In the course of this it can be used either alone or in combination with a fibrin glue acting as a haemostatic agent. Since the material in terms of its composition and general structure is similar to endogenous products, it has, inter alia, an excellent bio-compatibility, bio-degradability and bio-resorbability.

54 Claims, 7 Drawing Sheets

U.S. PATENT DOCUMENTS

| | | | |
|---|---|---|---|
| 4,683,142 | 7/1987 | Zimmermann et al. | 427/2 |
| 4,689,399 | 8/1987 | Chu | 530/356 |
| 4,690,684 | 9/1987 | McGreevy et al. | 623/12 |
| 4,704,131 | 11/1987 | Noishiki et al. | 623/66 |
| 4,720,512 | 1/1988 | Hu et al. | 523/112 |
| 4,725,671 | 2/1988 | Chu et al. | 530/356 |
| 4,760,131 | 7/1988 | Sundsmo et al. | 530/356 |
| 4,786,556 | 11/1988 | Hu et al. | 428/412 |
| 4,833,200 | 5/1989 | Noshiki et al. | 525/54.2 |
| 4,837,285 | 6/1989 | Berg et al. | 530/356 |
| 4,872,867 | 10/1989 | Joh | 604/269 |
| 4,882,148 | 11/1989 | Pinchuk | 424/423 |
| 4,911,926 | 3/1990 | Henry et al. | 424/426 |
| 4,932,942 | 6/1990 | Maslanka | 604/164 |
| 4,948,540 | 8/1990 | Nigam | 264/28 |
| 4,978,336 | 12/1990 | Capozzi et al. | 604/82 |
| 4,997,425 | 3/1991 | Shioya | 604/304 |
| 5,019,393 | 5/1991 | Ito et al. | 424/423 |
| 5,049,393 | 9/1991 | Noon et al. | 424/484 |
| 5,053,048 | 10/1991 | Pinchuk | 623/1 |
| 5,080,893 | 1/1992 | Goldberg et al. | 514/57 |
| 5,112,615 | 5/1992 | Ito et al. | 424/426 |
| 5,126,140 | 6/1992 | Ito et al. | 424/423 |
| 5,140,016 | 8/1992 | Goldberg et al. | 514/57 |
| 5,153,003 | 10/1992 | Kurihara et al. | 424/487 |
| 5,167,960 | 12/1992 | Ito et al. | 424/423 |
| 5,182,317 | 1/1993 | Winters et al. | 523/112 |
| 5,201,745 | 4/1993 | Tayot et al. | 606/151 |
| 5,209,776 | 5/1993 | Bass et al. | 106/124 |
| 5,213,580 | 5/1993 | Slepian et al. | 623/1 |
| 5,223,420 | 6/1993 | Rabaud et al. | 424/425 |
| 5,244,799 | 9/1993 | Anderson | 435/240.23 |
| 5,260,420 | 11/1993 | Burnouf-Radosevich et al. | 530/382 |
| 5,278,200 | 1/1994 | Coury et al. | 523/112 |
| 5,292,362 | 3/1994 | Bass et al. | 106/124 |
| 5,324,647 | 6/1994 | Rubens et al. | 435/180 |
| 5,364,622 | 11/1994 | Franz et al. | 424/94.64 |
| 5,376,376 | 12/1994 | Li | 424/443 |
| 5,376,692 | 12/1994 | Park et al. | 522/87 |
| 5,395,923 | 3/1995 | Bui-Khac et al. | 530/381 |
| 5,412,076 | 5/1995 | Gagnieu | 530/356 |
| 5,418,222 | 5/1995 | Song et al. | 514/21 |
| 5,447,724 | 9/1995 | Helmus et al. | 424/426 |
| 5,455,040 | 10/1995 | Marchant | 424/426 |
| 5,486,357 | 1/1996 | Narayanan | 424/78.17 |
| 5,521,280 | 5/1996 | Reilly et al. | 528/370 |
| 5,525,348 | 6/1996 | Whitbourne et al. | 424/423 |
| 5,541,167 | 7/1996 | Hsu et al. | 514/56 |
| 5,541,305 | 7/1996 | Yokota et al. | 536/21 |
| 5,567,806 | 10/1996 | Abdul-Malak et al. | 530/356 |
| 5,578,073 | 11/1996 | Haimovich et al. | 623/1 |
| 5,580,923 | 12/1996 | Yeung et al. | 525/54.1 |

FOREIGN PATENT DOCUMENTS

| | | |
|---|---|---|
| 0 187 894 A1 | 7/1986 | European Pat. Off. . |
| 0 213 563 B1 | 3/1987 | European Pat. Off. . |
| 0 262 890 A2 | 4/1988 | European Pat. Off. . |
| 0 369 764 A2 | 5/1990 | European Pat. Off. . |
| 0 372 969 A1 | 6/1990 | European Pat. Off. . |
| 0 479 615 A1 | 4/1992 | European Pat. Off. . |
| 0 485 210 A2 | 5/1992 | European Pat. Off. . |
| 0 534 178 A2 | 3/1993 | European Pat. Off. . |
| 0 562 864 A1 | 9/1993 | European Pat. Off. . |
| 0 611 571 A1 | 2/1994 | European Pat. Off. . |
| 0 592 242 A1 | 4/1994 | European Pat. Off. . |
| 2 448 900 | 1/1980 | France . |
| 38 41 397 C2 | 11/1992 | Germany . |
| WO 91/19519 | 12/1991 | WIPO A61L 25/100 |
| WO 92/15341 | 12/1992 | WIPO A61L 25/100 |
| WO 92/22312 | 12/1992 | WIPO A61K 37/02 |
| WO 93/19805 | 10/1993 | WIPO A61M 31/00 |
| WO 93/21971 | 11/1993 | WIPO A61L 33/00 |
| WO 94/02182 | 2/1994 | WIPO A61L 25/00 |
| WO 94/22503 | 10/1994 | WIPO A61L 25/00 |
| WO 96/22115 | 7/1996 | WIPO A61L 31/00 |

OTHER PUBLICATIONS

Use of Thrombin and Fibrinogen in Skin Grafting, Apr. 1, 1944, Lieutenant Eugene P. Cronkite et, al., J.A.M.A.

Preparation and Properties of Serum and Plasma Proteins. IX Human Fibrin in the Form of an Elastic Film, Feb. 1947, John D. Ferry and Peter R. Morrison, Am. Chem Soc. J.

Fibrin Gel Limits Intra–Abdominal Adhesion Formation, Sep. 1992, Gary W. Chmielewski, et al., Am. Surgeon.

Molecular Biology of Fibrinogen and Fibrin, 1983, Jodn D. Ferry, NYAS.

Fibrin as a Haemostatic In Cerebral Surgery, 1915, Ernest G. Grey, Surg., Gyn and Obst.

Plasma Clot Suture of Nerves, 1943, I.M. Tarlov, M.D., et al., Archives of Surg.

The Prevention and Treatment of Intestinal Adhesions, May 1960, John E. Connolly, M.D., et al., Intl Abst. of Surg.

The Binding of Human Fibrinogen to Native and Fraction Fibrins and the Inhibition of Polymerization of a New Human Fibrin, 1964, A.L. Copley and B.W. Luchini, Life Sciences.

Stable Complex of Fibrionogen and Fibrin, May 20, 1966, Takeru Sasaki, et al., Science.

An Evaluation of the Bionite Hydrophili Contact Lens for Use in a Drug Delivery System, Sep. 1972, Yvonnet Maddox, B.S. and Howard N. Bernstein, M.D., Annals of Ophthal.

Treatment of Stress Incontinence by a Fibrin Bioplas, Jan. 1975, Bela Horn, et. al., Brit. J. Ob. & Gyn.

Effect of a Biologic Glue on the Leakage Rate of Experimental Rectal Anastomoses, May 1982, Hisashi Oka, MD., et al., Am. J. Surg. Canada.

In Vitro Properties of Mixtures of Fibrin Seal and Antibiotics, Jan. 1983, H. Ridi, G. Schlag. et. al., Biomats.

Fibrin Gels and Their Possible Implication for Surface Hemorheology in Health and Disease, 1983, Birger Blomback and Masahisa Okada, Ann. N.Y. Acad. Science.

History Background Application Techniques and Indication of "Fibrin Sealing" in Modern Surgery, Jan. 1985, Lukas Giovanettoni, Immuno U.S., Inc.

Studies on Prevention of Intra–Abdominal Adhesion Formation by Fibrin Sealant, May 27, 1985, Svend Lindenberg, et al., Acta Chir Scand.

Localized Prevention of Postsurgical Adhesion Formation and Reformation with Oxidized Regenerated Cellulose, 1987, Takao Shimanuki, et al., J. of Biomed. Mats. Research.

The Use of Sprayed Fibrin Glue for Face Lifts, 1987, D. Marchac E. Pugash and D. Gault, Euro J. Plast Surg.

Mediastinal Fibrin Glue: Hemostatic Effect and Tissue Response in Calves, Nov. 7, 1988, J,W. Baker, MD., et al., Ann Thorac Surg.

Reduced Human Peritoneal Plasminogen Activating Activity: Possible Mechanism of Adhesion Formation, Apr. 1989, J.N. Thompson, et al., Br. J. Surg.

Fibrin Glue Inhibits Intra–abdominal Adhesion Formation, Jun. 10, 1990, Christian de Virgilio, et al., Arch. Surg.

Die Anwendung des Fibrinklebers zur Prophylaxe und Therapie intraabdomineller Adhasionen, 1990, W. Brands, Th. Diehm, et al., Der Chirurg.

The Need for Intensive Study of Pericardial Substitution After Open Heart Surgery, 1990, Shlomo Gabbay, Trans Am Soc. Artif. Intern Organs.

Dura Covered with Fibrin Glue Reduces Adhesions in Abdominal Wall Defects, Nov. 1, 1990, F. Schier, et al., Eur. J. Pediatr. Surg.

The Effect of Fibrin Glue and Peritoneal Grafts in the Prevention of Intrapertioneal Adhensions, 1990, J.F.H. Gauwerky, et al., Arch. Of Gyn. & Obst.

Effect of Fibrin Sealant on Tubal Anastomosis and Adhesion Formation, Jul. 1991, Togas Tulandi, M.D., Fertility and Sterility.

Aleration in Pericardial Adhesion Formation Following Pretreatment with Fibrin Glue, 1991, Douglas H. Joyce, et al., J. of App. Biomet.

Prophylaxis of Pelvic Sidewall Adhesions With Gore–Tex Surgical Membrane, a Multicenter Clinical Investigation, 1992, The Surgical Membrane Study Group, Fertility & Sterility.

Effectiveness of Two Barriers at Inhibiting Post–radical Pelvic Surgery Adhesions, 1993, F.J. Montz, et al., Gyn. Onc.

Inhibition of Intra–abdominal Adhesions: Fibrin Glue in a Long Term Model, 1993, Barry B. Sheppard, M.D. et al., Am. Surg.

Properties and Prevention of Adhesions Applications of Bioelastic Materials, 1993, D.W. Urry, et al., Mat. Res. Soc. Symp. Proc.

Expanded–polytetrafluoroethylene But Not Oxidized Regenerated Cellulose Prevents Adhesion Formation and Reformation in a Mouse Uterine Horn Model of Surgical Injury, 1993, A.F. Haney, M.D., Fertility & Sterility.

Fibrin Sealant Adhesive Systems: A Review of Their Chemistry, Material Properties and Clinical Applications, Apr. 1993, David H. Sierra, J. of Biomat. Appl.

Prevention of Postoperative Adhesions in the Rat by In Situ Photopolymerization of Bioresorbable Hydrogel Barriers, Jan. 1994, Jennifer L. Hill–West, et al., Obstetrics & Gynecology.

Fibrin Sealant in Laparoscopi Adhesion Prevention in the Rabbit Uterine Horn Model, Aug. 1994, PierAndrea De Iaco, M.D., et al., Fertility & Sterility.

Prevention of Surgical Adhesions Using Aerosoled Biodegradable Polyesters, Apr. 1994, SM Fujita, et al., Soc. For Biomat.

Tissue Adhesives in Wound Healing, May 1994, Dale S. Feldman and David H. Sierra, Unpublished Manuscript.

Adhesion Reduction in the Rabbit Uterine Horn Model Using an Absorbable Barrier, TCD–7, Jan. 1997, Cary B. Linsky, Ph.D., et al., J. of Reproductive Med.

FIG. IA
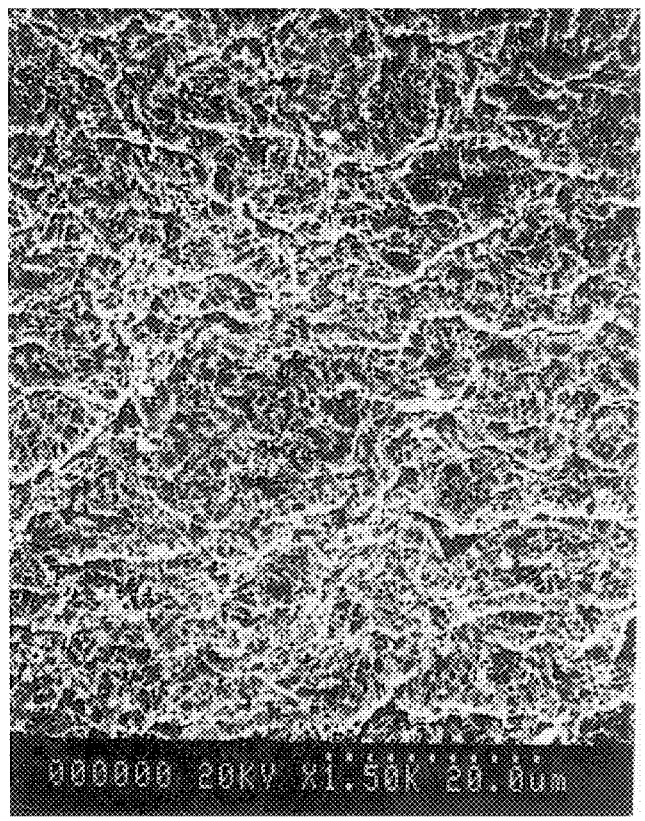
FIG. IB
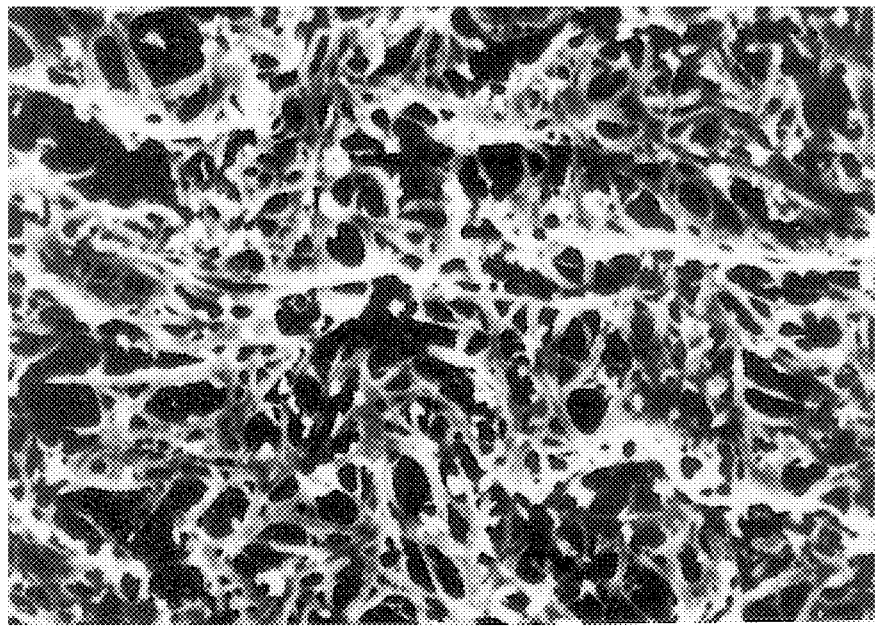

SEQUENTIAL APPLICATION
SINGLE COATING

LEGEND

| 1ST LAYER

| 2ND LAYER t = APPLICATION TIME

SEQUENTIAL APPLICATION
DOUBLE COATING

LEGEND

| 1ST LAYER

| 2ND LAYER t = APPLICATION TIME

SIMULTANEOUS APPLICATION
SINGLE COATING

LEGEND

| 1ST LAYER

| 2ND LAYER t = APPLICATION TIME

SIMULTANEOUS APPLICATION
DOUBLE COATING

LEGEND

| 1ST LAYER

| 2ND LAYER t = APPLICATION TIME

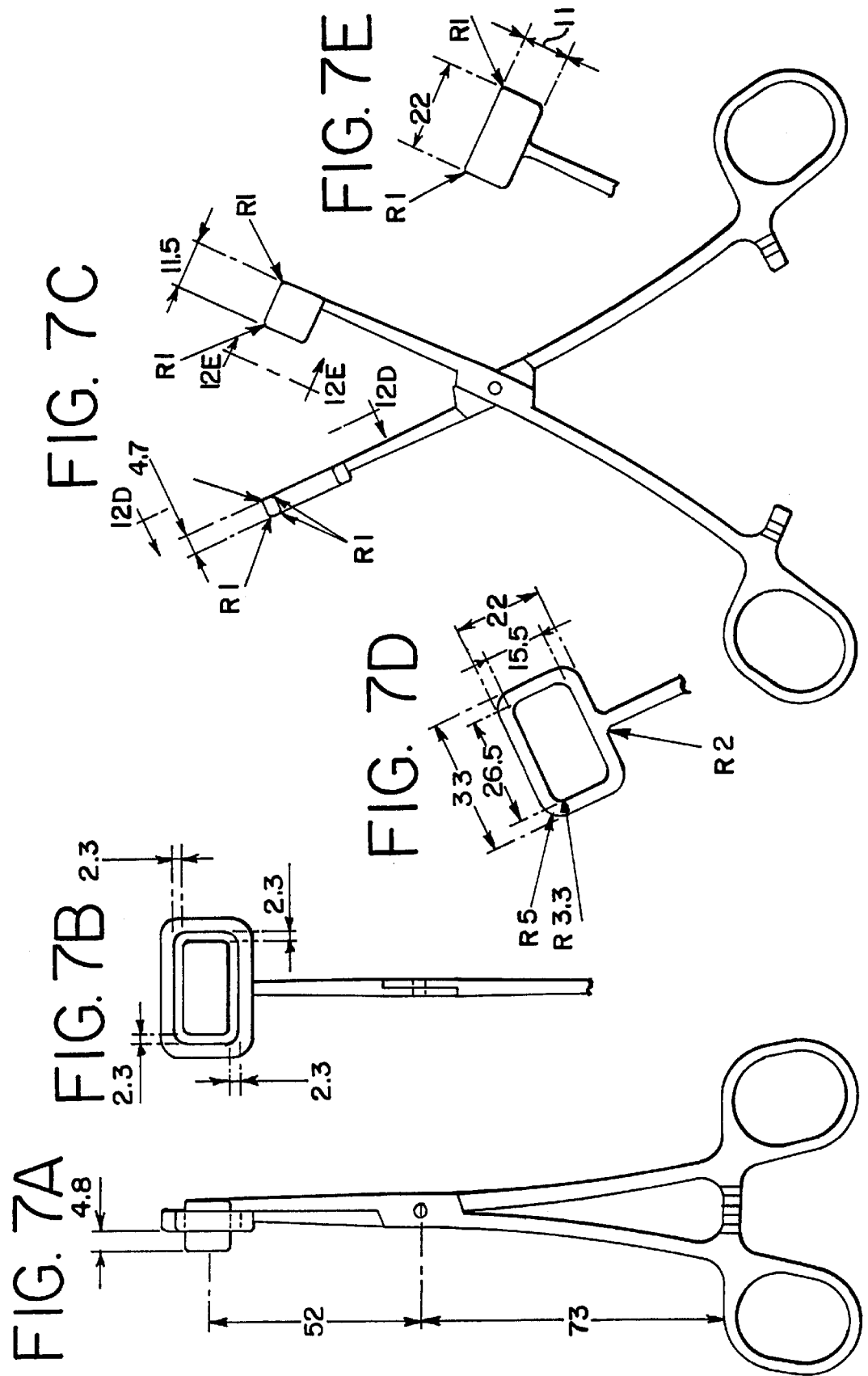

METHOD OF USING CROSS-LINKED FIBRIN MATERIAL

This application is a 371 of PCT/EP96/00160, filed Jan. 16, 1996.

The invention relates to a self-supporting sheet-like material of cross-linked fibrin and to processes for making said material. The invention also relates to the use of said material and of fibrin glues/sealants for the treatment of internal traumatic lesions, particularly for the prevention of post-operative adhesion formation.

One of the major problems in intra-abdominal surgery is the avoidance of post-operative adhesions. It is well-known that adhesions contribute to pain, immobility, retarded wound healing, and in particular to intestinal obstruction which even may be life-threatening. In the field of gynecological surgery, post-surgical adhesions involving female reproductive organs may result in infertility.

Each surgical procedure necessarily produces a wound such as in laparoscopy, where the abdominal wall is opened for an inspection of the abdominal cavity. Physiologically, the process of wound closure then starts when bleeding ceases upon formation of a haemostatic clot at the places, where blood vessels are injured. The clot, at first comprising mainly platelets, is solidified by a fibrin network resulting from the activation of an enzyme cascade involving thrombin, factor XIII and calcium. Further steps on the way to the sealing of the wound are retraction of the haemostatic clot, invasion of various cell types including fibroblasts into the wound area and eventually the lysis of the fibrin network. Adhesions are thought to be formed when the fibrin clot covering an injury comes into contact with an adjacent surface and the new connective tissue produced by the fibroblasts "glues" the two surfaces together.

The problems associated with adhesions often require a further operative procedure for removing/lysing the adhesions, called adhesiolysis, which, like the first operation, principally bears the risk that adhesions are caused. Accordingly, the prevention of adhesion formation is mandatory. Among the different approaches for prevention of adhesion formation, one involves the use of materials as a physical or bio-mechanical barrier for the separation or isolation of traumatized tissues during the healing process. Both synthetic materials and natural materials have been used as a barrier to adhesion formation. Permanent, inert implants like Gore-Tex surgical membranes consisting of expanded polytetrafluoroethylene (PTFE) generally require a second operative procedure to remove them, while others such as surgical membranes of oxidized regenerated cellulose are biodegradable, but are thought to elicit an inflammatory response ultimately leading to adhesion formation (A. F. Haney and E. Doty, *Fertility and Sterility* 60, 550–558, 1993). Other barrier materials that have been proposed for the prevention of adhesions include elastin-derived bioelastic matrixes (D. W. Urry et al., *Mat. Res. Soc. Symp. Proc.* 292, 1993) and mucopolysaccharide films (T. Matsuda et al., *ASAIO Journal* 38, M 154–157, 1992). However, complete prevention of adhesion formation using these two latter materials has not been reported so far.

On the other hand, (fluid) fibrin sealants/glues are well-known in the art for use in haemostasis, tissue sealing and wound healing and have been commercially available for more than a decade. Fibrin glues imitate the last step of the coagulation cascade and are usually commercialized as kits comprising two main components. The first component is a solution comprising fibrinogen and factor XIII, while the second component is a thrombin-calcium solution. After mixing of components, the fibrinogen is proteolytically cleaved by thrombin and thus converted into fibrin monomers. In the presence of calcium, Factor XIII is also cleaved by thrombin into its activated form (FXIIIa). FXIIIa cross-links the fibrin monomers to a three-dimensional network commonly called "Fibrin Gel". In order to avoid that a premature coagulation prevents/impairs the application of the fibrin glue, the two components are either mixed by means of special devices immediately before application to the recipient surface or directly in sine. Thus, the polymerization/gelation step is exclusively performed in sitar.

Since the "Fibrin Gel" resulting from the application of fibrin glues is an optimal substrate for the ingrowth of fibroblasts and their subsequent elaboration of connective tissue substances, fibrin glues have generally been considered to have adhesion-promoting rather than anti-adhesive properties.

It has now surprisingly been found that a self-supporting sheet-like material of cross-linked fibrin can be used as a bio-mechanical barrier in the treatment of internal traumatic lesions, particularly for the prevention of adhesion formation as a post-operative complication. To that end, those of skill in the art will recognize that the bio-mechanical barrier is generally useful in all fields of surgery. Examples, which are not intended to be limiting, include obstetrics and gynaecology, abdominal surgery, orthopedic surgery, ocular surgery and cardiovascular surgery. Normally, the barrier is in the form of a film which, upon external preparation, is placed during the surgical procedure over one or between two surgically traumatized surfaces to isolate it and separate them, respectively, and to allow independent healing without the formation of adhesions.

In accordance with this invention, a self-supporting sheet-like material of cross-linked fibrin is provided as is defined in the claims. Furthermore, processes for the preparation of said material as defined in the claims are also provided. In still another aspect of the present invention, the use of said material in medicine and/or veterinary medicine is provided. In addition, the use of said material for the preparation of a medicament for the treatment of internal traumatic lesions as defined in the claims is provided. In a further aspect of the present invention, a combined use of a first fibrin glue acting as a haemostatic agent and of a second fibrin glue acting as a bio-mechanical barrier for the preparation of a medicament for the treatment of internal traumatic lesions as defined in the claims is provided. Further embodiments of the invention are also defined in the claims.

For the sake of convenience, the term "fibrin film" is used in the following to refer to a self-supporting sheet-like material of cross-linked fibrin. For the purposes of the invention, the fibrin film is composed of the same constituents as the fibrin glues on the market, i.e. mainly fibrinogen, thrombin, factor XIII and calcium.

Particularly advantageous is that the fibrin film does not considerably slip or move upon placement so that no fastening, like sutures, are required in the course of surgery. Due to its inherent mechanical properties, the fibrin film allows a tight cover over the traumatized tissue. Moreover, the fibrin film in terms of its composition and general structure is similar to the natural products formed upon injury in the human or animal body and, thus, they fulfill prime requirements an ideal surgical membrane would have, such as superior biocompatibility, biodegradability and bioresorbability. As a result and by marked contrast to barriers of inert materials like expanded PTFE, a bio-mechanical barrier made of fibrin disappears 'by itself' after exerting its function so that no second surgical procedure for removal is required; in the animal model (rat) described below this usually occurs within ten days after the application of the fibrin film. Furthermore, it is appreciated that the fibrin film does not provoke any major side effects to the body.

In accordance with preferred embodiments of the invention, a self-supporting sheet-like material of cross-linked fibrin is provided, wherein said material has a regular pore size. The fibrin film of the invention has a dense, regular and homogenous structure within its entire volume as shown by Scanning Electron Microscopy (SEM). The pore size of the fibrin film is 'regular' in the sense of varying only in a range of a few micrometers. It has been found that such a fibrin film is particularly effective in preventing adhesion formation.

On the other hand, according to experiments by the inventors, fibrin films having a more open or even irregular or non-homogenous structure including larger holes are not effective in this respect. Without being bound to a theory, this may be explained as follows. Such foam-, sponge- or fleece-like structures may allow the retention of blood set free during surgery and may further allow the ingrowth of fibroblasts, thus promoting endogenous fibrin formation accompanied by adhesion formation. Accordingly, such fibrin films, in particular in their dry state, may be useful in haemostasis to soak up the exudate of the injury. However, in anti-adhesion therapy, non-haemostatic fibrin films with non-adhesive properties are generally desired.

The fibrin film of the invention is insoluble in water and in the wet form may contain up to 92% by weight of water. Irrespective of being in hydrated (wet) or rehydrated state (e.g. after a previous drying step for storing), this fibrin film has a high mechanical strength, is by itself self-supporting and is yet soft. Thus, the fibrin film of the invention is easy to handle allows cutting, rolling and also suturing, if required. The self-supporting property of the fibrin film is reinforced by drying. The dry form of the fibrin film may be commercialized as part of a kit and is then to be rehydrated before use in surgery with appropriate solutions of e.g. water, calcium chloride, but also buffered solutions containing drugs.

Preferably, for the purposes of the present invention in certain embodiments, the pore size of the barrier material is below about 5 µm, preferably below about 1 µm, to prevent fibroblasts from intruding or penetrating. As noted above, in the course of normal wound closure, fibroblasts migrate into the fibrin clot network and the developing granulation tissue, where they produce i.a. collagen and thus contribute to the ultimate formation of a scar tissue. In order to avoid that the substances produced by the fibroblasts contribute to glue, an injured surface and an adjacent surface or two injured surfaces together, the inventors propose to isolate or separate the injured surface(s) by using fibrin barrier material having a pore size, preferably a 'regular' pore size in the sense of the present invention, of below 5 µm, preferably of below 4 µm, preferably of below 3 µm, preferably of below 2 µm and most preferably of below 1 µm. In fact, experiments by the inventors described below demonstrate that by using such barriers the formation of adhesions can be prevented completely.

Usually, fibrin film in accordance with the invention is made of a single layer which, for the purpose of preventing adhesion formation, has a closed structure, but may also have an open structure for other applications. Moreover, the inventors propose a fibrin film comprising two or more layers. At least one layer, either as an outer layer or an intermediate layer, should have a closed structure ensuring the rigidity and/or the barrier function of the multi-layered fibrin film, whereas other layers having a open structure may work as a drug delivery system.

In preferred embodiments, the thickness of the fibrin barrier material is at least 20 µm when the barrier is in the wet state. Preferably the thickness is about 20–2000 µm, and most preferably up to 5000 µm, although it is believed that even material with a thickness of less than 20 µm may be suitable for the purposes of the invention.

In still further embodiments of the present invention, the fibrin film further comprises less than 5% by weight of fibrinogen, preferably less than 4% by weight of fibrinogen, preferably less than 3% by weight of fibrinogen, preferably less than 2% by weight of fibrinogen, and most preferably less than 1% by weight of fibrinogen, in terms of the total dry weight of the fibrinogen plus fibrin each time. The fibrin film of the invention is usually made by catalytic conversion of fibrinogen to fibrin. Generally speaking, the lower the amount of residual fibrinogen, the better the non-adhesive properties of the fibrin film, since fibrinogen in vivo may promote fibrin formation and thus adhesion formation. Ideally, the fibrinogen to fibrin conversion should be complete, i.e., the fibrin film contains no residual fibrinogen. For the purpose of determining the fibrin and the fibrinogen content of the fibrin film, the methods of SDS-Page (SDS-Gelelectrophoresis) may be used.

It is preferred in certain embodiments that the fibrin film further comprises one or more disinfectants, preferably methylene blue, and/or one or more drugs selected from antibiotics, fibrinolytic agents and biological response modifiers, in particular cytokines and wound repair promoters, preferably in an amount up to 1% by weight in terms of the total dry weight of fibrin plus fibrinogen. Examples of fibrinolytic agents include t-PA, $\mu$-PA, streptokinase, staphylokinase, plasminogen and the like. These compounds promote fibrinolysis and thus can be used for controlling the rate of the degradation of the fibrin film in vivo. The term "biological response modifiers" is meant to refer to substances which are involved in modifying a biological response, such as wound repair, in a manner which enhances the desired therapeutic effect. Examples include cytokines, growth factors and the like. Due to its intrinsic mechanical properties, the fibrin film of the invention does not require any additional cross-linking agent which may exert any toxical effects to the human or animal body.

The present invention is also concerned with processes of preparing a self-supporting sheet-like material of cross-linked fibrin, which processes are defined in the claims.

Accordingly, in certain embodiments of the invention, a process of preparing a self-supporting sheet-like material of cross-linked fibrin is provided, which process comprises the steps of:

(a) simultaneously mixing a stream of a first, fibrinogen-containing solution with a stream of a second, thrombin-containing solution;

(b) applying the obtained mixture to a solid support; and (c) incubating the mixture to form the desired material.

In order to obtain a mixture as homogenous as possible (and thus a homogenous final product) in step (a), a stream of a first, fibrinogen-containing solution is simultaneously mixed with a stream of a second, thrombin-containing-solution. The first and/or the second solution may further comprise disinfectants and/or drugs selected from antibiotics, fibrinolytic agents and biological response modifiers, in particular cytokines and wound repair promoters. Preferably, equal volumes of the first and the second solution are mixed. In case the different volumes of the first and the second solution should be simultaneously mixed, it will be known in the art which measures have to be taken in order to ensure that a homogenous mixture is obtained.

Those of skill in the art will readily recognize that the mixing in step (a) can be performed using commercially available dual syringe devices. A suitable commercial product is e.g. DUPLOJECT® of IMMUNO in Heidelberg, Germany. Accordingly, the two solutions are separately filled into the two syringes being held together by a Y-piece. The solutions are mixed at the end of the Y-piece, when the contents of the syringe are expressed. Alternatively, suitable spraying devices known in the art may be used. The resulting mixture is spread over the surface of a solid support, for example a petri dish and the like, which is tilted to cover the entire surface as far as possible before the formation of the three-dimensional fibrin network starts. Using this preparation mode, fibrin films made with low concentrations of thrombin can easily be obtained. With higher concentrations of thrombin, a faster clotting time and thus a rapidly increasing viscosity of the mixture are observed as main limitations for the mixing procedure described above. Accordingly, for higher thrombin concentrations, care has to be taken that the mixture formed in accordance with step (a) is uniformly distributed over the surface of the solid support from the beginning, so as to yield a homogenous final product in step (c).

Step (c) preferably requires that the mixture applied to the solid support is allowed to set completely, i.e., a conversion of fibrinogen to fibrin as complete as possible is obtained. Preferably, completion of the conversion of fibrinogen to fibrin is achieved by incubation of the solid support at the physiological temperature, i.e., 37° C. for 1–200 minutes. It will be appreciated that the incubation may also be extended up to 24 hours and more. In this respect it is noted that the invention shall also cover those products, where the fibrinogen to fibrin conversion has not reached completion.

The components of the first and second solution can be prepared from plasma by conventional precipitation and purification steps. When the patient to be treated is a human being, human plasma will be preferred. The source of the plasma may be either pooled donor blood and single donor blood obtainable from blood centers, respectively. Care should be taken that state of the art controls are performed to detect viral contamination. During the process of manufacturing, the products may be sterilized by standard techniques as well. In order to avoid any risk of contamination, the components could be prepared from pre-operative autologous blood donation. It will be understood that the components of the first or the second solution or their functional analogues may also be prepared by using the methods of molecular genetics.

Conveniently, in the light of the present disclosure, commercially available two-component fibrin glue kits may be used for the preparation of the fibrin film of the present invention. The required constituents are usually contained in the kits in the form of dry concentrates and have to be reconstituted as per the technical data sheet provided with the respective kit. The desired thrombin concentration is prepared by diluting an aliquot of the reconstituted thrombin solution with sterile calcium chloride solution, preferably 20 mM calcium chloride.

The inventors propose that the fibrin film of the invention may also be obtained from one vial containing all the required components, where the catalytic agents for the fibrinogen-fibrin conversion and the cross-linking of soluble fibrin, respectively, are inactivated and the polymerization is only started by induction through a change in pH, ionic strength, light and the like after the content of said vial had been applied to the solid support. By way of example, photo-sensitive inhibitors of thrombin and thrombin-like molecules could be used for this purpose. The fibrin film of the invention may also be prepared in accordance with Copley and Luchini, (*Life Sciences* 3, 1293–1305, 1964) and Sasaki et al. (*Science* 152, 1069–1071, 1966) by starting from soluble fibrinogen-fibrin monomer complexes precipitated in the cold, redissolved at high temperature and which are then cross-linked with F XIII and calcium.

In accordance with the invention, the first solution preferably contains fibrinogen and factor XIII (10–40 IU/ml). The concentration of fibrinogen is expressed as the total protein concentration (about 90–140 g/l) and the percentage of clottable protein comprised therein. The inventors prefer the percentage of clottable protein to be at least 80% and preferably equal to or greater than 90%. Of course, those of skill in the art will recognize that a variety of other constituents may be included in the first solution, for example albumin, plasminogen and tensides. The second solution preferably comprises 1–300 IU/ml thrombin or more than 300 IU/ml thrombin (depending on the desired biophysical parameters of the material to be obtained) and calcium in a concentration of up to 45 mM. For simplification, the thrombin concentration normally given in IU/ml, will in the following frequently be indicated in IU, in particular in the Tables.

As an alternative, in particular for the purpose of preparing a fibrin film with a higher concentration of thrombin, the inventors propose a process comprising the steps of:

(a) applying a first, aqueous, fibrinogen-containing solution onto a solid support;

(b) removing the water until dryness while forming a sheet-like fibrinogen material;

(c) applying to the sheet-like fibrinogen material a second, thrombin-containing solution; and (d) incubating to form the desired material.

Whereas the specific steps of this process differ from those of the previously described process for the preparation of a fibrin film, the same first and second solutions may be used. In a preferred embodiment of said process, equal volumes of the first and the second solution are used in steps (a) and (c).

In order to obtain a final product having a regular thickness and a homogenous structure the first, aqueous, fibrinogen-containing solution should be uniformly distributed over the entire solid support. Step (b) requires that the solvent of the first solution, i.e. water, is removed until dryness in order to obtain a sheet-like fibrinogen material. Preferably, removal of water is performed by air drying, freeze drying, or drying under increased temperature and/or reduced pressure. The obtained sheet-like fibrinogen material has microcavities as shown by SEM and, thus, a high absorptive capacity for fluids. Said material is converted into a self-supporting sheet-like material of cross-linked fibrin upon rehydration by means of the addition of a second, thrombin-containing solution, which optionally comprises disinfectants and/or drugs like antibiotics, fibrinolytic agents, biological response modifiers and the like.

According to step (d), the solid support and, thus, the intermediate to product of step (c), is incubated to form the self-supporting sheet-like material of cross-linked fibrin, i.e. the final product. Preferably, step (d) comprises incubating the solid support at 37° C. for about 20 minutes (with material of low thickness) to about 200 minutes (with material of high thickness) to complete the conversion of fibrinogen to fibrin. It will be appreciated that the incubation to form the final product may be extended to up to 24 hours and more.

It has been found that, with this process, the thickness of the fibrin film is independent of the concentration of the thrombin solution used. The fibrin film obtained has a high mechanical strength and can be cut, bent, rolled and sutured, and has a regular surface. In terms of the process, a particular advantage resides in that it is not dependent on the clotting time. That is, no premature clotting may occur, since the first and the second solution are separately applied to the solid support.

It is, of course, recognized that the preliminary process steps of the two processes described above are preferred laboratory procedures that might be readily replaced with other procedures of equivalent effect.

Generally speaking, the main determinants in influencing the fibrin network structure and its biological and biophysical characteristics include the concentrations of thrombin, fibrinogen and factor XIII, and, of course, the temperature at which the polymerization is performed. The fibrinogen concentration and, in a large measure, the clottable protein concentration is proportional to the tensile strength, while the concentration of factor XIIIa which covalently cross-links the fibrin monomers influences the elasticity of the fibrin network.

However, the thrombin concentration plays a key function for controlling fibrin network formation. That is, the biopolymer structure is inversely related to the thrombin concentration, while keeping the same regular and uniform structure at each concentration of thrombin. At low concentrations of thrombin, there is a slow fibrinogen conversion associated with a slow fiber growth, thus leading to the formation of a fibrin structure with thick fibers and large pore size (>1 $\mu$m). In other words, a low thrombin concentration leads to a long clotting time and larger pores. On the other hand, high concentrations of thrombin result in shorter clotting times producing a tight material with thinner fibrin fibers and smaller pore size (<1 $\mu$m). This effect can be demonstrated by using standard scanning electron microscopy (SEM). While FIG. 1 shows the network of a fibrin film developed with a low thrombin concentration (3 IU) having a pore size of greater than 1 $\mu$m (about 3–4 $\mu$m), FIG. 2 shows a fibrin film made with a high thrombin concentration (300 IU) having a pore size below 1 $\mu$m (about 0.2 $\mu$m). For comparison, FIG. 3 shows a representative human fibrin clot structure. In the human haemostatic clot, the presence of cells drastically opens the three-dimensional structure of the network. Such an opened and irregular structure is physiologically favorable to fibroblast migration into the fibrin clot network during the normal wound healing process. It is apparent from the figures that by varying the thrombin concentration, fibrin networks with low or high pore size are obtainable. For the use of the fibrin material as a bio-mechanical barrier in accordance with the present invention, the thrombin concentration is preferably adjusted to obtain a fibrin network structure with a pore size excluding fibroblast penetration. The fibrin material produced in accordance with the invention may be examined by standard SEM and further be tested in the animal model described herein.

In view of these findings, the inventors propose that a fibrin film with a highly ordered structure having a 'low pore size' is useful as a bio-mechanical barrier to avoid contacts between adjacent injured surfaces. Additionally, it is proposed to use a fibrin film with a highly ordered structure having 'relatively large pores' as a matrix for cells and molecules for the achievement of hemostasis and wound repair.

This is all the more important as the inventors using the animal model described below, have found that the development of adhesion requires blood, peritoneal trauma, and approximation/contact of injured surfaces.

Under consideration of these three factors, in certain embodiments haemostasis and wound repair is addressed by applying a single layer of fibrin glue to the injury site(s), while the separation/isolation of the injured surface(s) is achieved by using a bio-mechanical fibrin barrier, either applied as a second layer on top of the first layer of the fibrin glue, or simply as a self-supporting sheet placed between the adjacent injury sites or between the site of the injury and the adjacent uninjured tissues. The inventors have discovered that an important parameter to be taken into account in using such a combination of a haemostatic agent/wound repair promoter and a bio-mechanical barrier is the time required for complete conversion of fibrinogen to fibrin. Specifically, it has been found that the layer of the fibrin glue and respectively the last layer, if more than one layer is applied to an injured surface, should be allowed to set until the conversion of fibrinogen to fibrin is complete. By way of example, when fibrin glue is applied simultaneously to two injured surfaces such as caecum and peritoneal wall in order to form a single layer each time, and the surfaces come into contact with each other before the fibrinogen-fibrin conversion is complete, it may occur that these surfaces are glued together, i.e., that adhesions are formed.

This means that the surface state of the different interfaces and their relationships are very important in the prevention of adhesions. As a general guidance, the inventors propose to allow undisturbed setting after application of the respective last external layer of fibrin glue until the conversion of fibrinogen to fibrin is complete. This does not apply to the fibrin film of the invention, since this is allowed to set completely in vitro before application. Of course, although detailed experimental protocols are described hereinafter, those of skill in the art will appreciate that the specific time requirements may vary depending on the particular patient, the type of injury and the handling, and is thus apparently also a matter of clinical experience. However, in vitro methods are known in the art for monitoring the fibrinogen-fibrin conversion. By way of example this can be followed by monitoring turbidity which is the measure of the optical density of fibrin networks developed in a cuvette with a path of one centimetre at 800 nm (cf. G.A. Shah et al., *Thrombosis Research* 40, 818–188, 1985). In accordance with this method it is possible to determine in vitro the time required for complete fibrin formation at a given thrombin concentration. This provides an estimate of the minimum time required for complete setting after application of the last external layer(s). It is believed that, based on the present disclosure, one of average skill in the art could define a protocol for use of a dedicated fibrin glue, its mode and type of application, so that the requirements for surgeons with respect to the timing and the technical devices are met.

In accordance with the general guidelines described above, a preferred embodiment called "double coating" comprises the application of a first fibrin glue with a low concentration of thrombin to work as haemostatic agent and/or tissue repair promoter, and of a second fibrin glue with a to high concentration of thrombin playing the role of a bio-mechanical barrier which entirely covers the injury and the first coating formed upon application of the first fibrin glue. Preferably the first fibrin glue has been made by mixing of the above-described fibrinogen-containing solution with an equal volume of a thrombin-containing solution comprising less than 1000 IU thrombin, preferably less than 150 IU. The fibrin glue has been preferably made by mixing said fibrinogen-containing solution with an equal volume of a thrombin-containing solution of at least 50 IU thrombin, preferably of at least 150 IU thrombin, and most preferably of least 300 IU thrombin. Of course, it will also be possible to apply more than two layers as long as the last layer plays the role as a bio-mechanical barrier preventing fibroblast proliferation between the covered lesion and the adjacent surfaces.

In another preferred embodiment of the invention called "sandwich method", a fibrin glue layer covering the injured surface(s) is used as haemostatic agent and wound repair promoter, while a fibrin film, in i.e., a self-supporting sheet-like material of cross-linked fibrin being placed between the injured surface and an adjacent uninjured surface, or between two injured surfaces, acts as a bio-mechanical barrier. The fibrin glue is preferably produced by mixing of a first, fibrinogen-containing solution with an equal volume of a thrombin-containing solution comprising 1–300 IU/ml thrombin, preferably at least 20 IU/ml thrombin and most preferably at least 100 IU/mi thrombin. The fibrin film is made of at least 4 IU/ml thrombin, preferably of at least 20 IU/ml thrombin, and most preferably of at least 300 IU/ml thrombin. It will, of course, be recognized that the fibrin film can also be used in combination with a double coating as described above.

The above-described embodiments may be used either alone or in to combination with other embodiments.

BRIEF DESCRIPTION OF THE DRAWINGS

These and other details as well as further preferred embodiments and advantages of the invention will become apparent from the following Examples, the appended claims and the drawings which show in FIG. 1 Scanning electron microscopy (SEM) of a fibrin film made of 3 IU of thrombin (mag. 1,5 K and 5.0 K). The pore size is about 3–4 $\mu$m.

The fibrin films 3 IU and 300 IU were prepared by using the components contained in a standard fibrin glue kit and adjusting the two different thrombin concentrations of 3 IU/ml and 300 IU/ml by diluting the reconstituted thrombin solutions with 20 mM $CaCl_2$. The samples were casted in petri dishes in accordance with the procedure described in Example 1 and incubated at 37° C. for 1 hour.

Figure 3A:
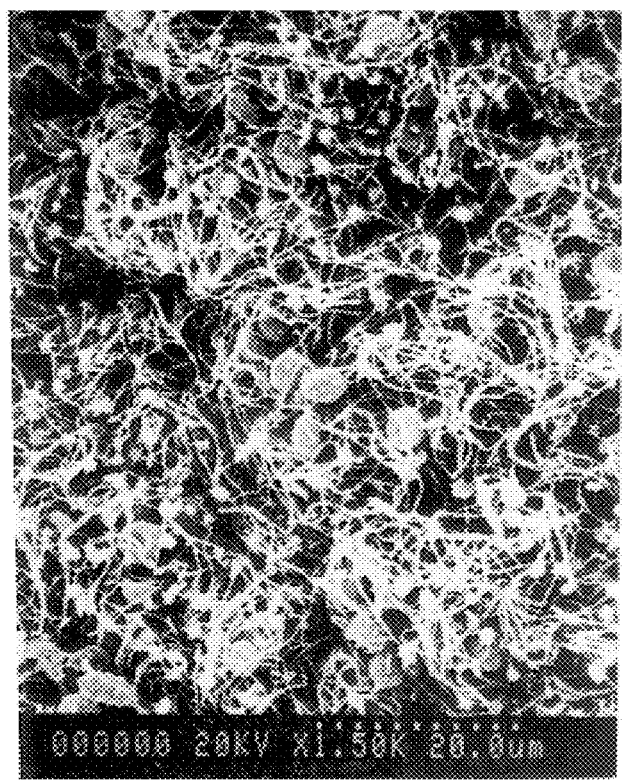
Figure 3B:
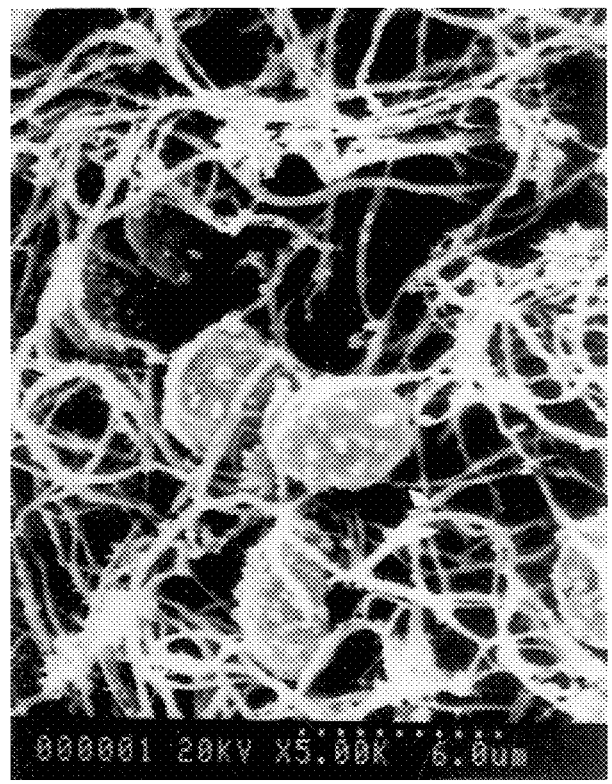

FIG. 3 SEM observation of a blood clot obtained by mixing 100 $\mu$l of autologous blood with 100 $\mu$l of 20 mM $CaCl_2$ (×1,5 K, ×5.0 K).

Figure 2A:
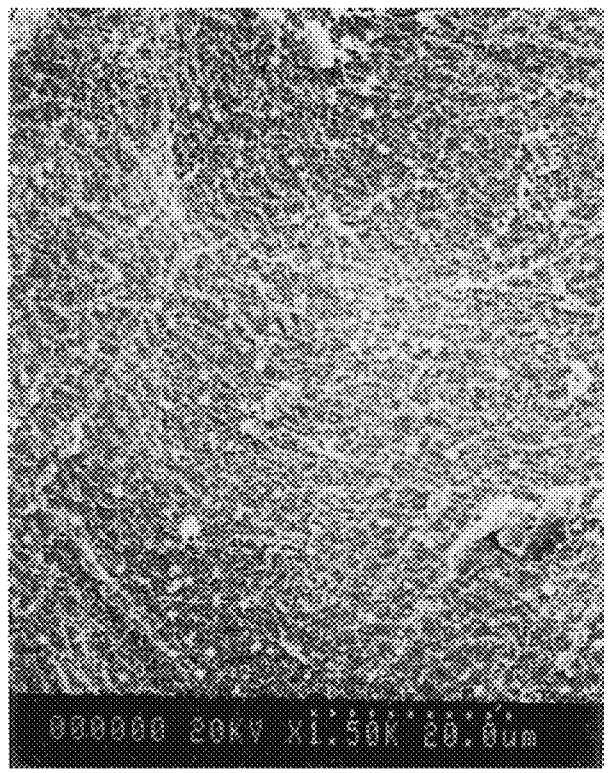
FIG. 2 SEM of fibrin film made with 300 IU of thrombin (×1,5 K, ×5.0 K). The pore size is about 0.2 $\mu$m.
Figure 2B:
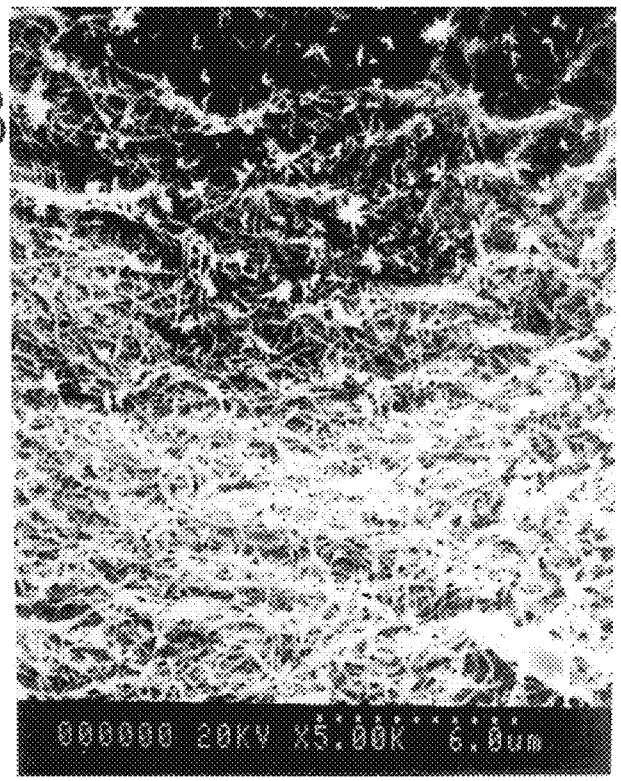

The samples shown in FIGS. 1–3 were processed for SEM in accordance with standard protocols.

The length of the dotted line in the text of FIG. 1–3 corresponds to 20 $\mu$m (×1,5K) and 6.0 $\mu$m (×5.0K), respectively.

Figure 4A:

FIG. 4A Fibrin film in accordance with Example 1, containing methylene blue as disinfectant.

Figure 4B:
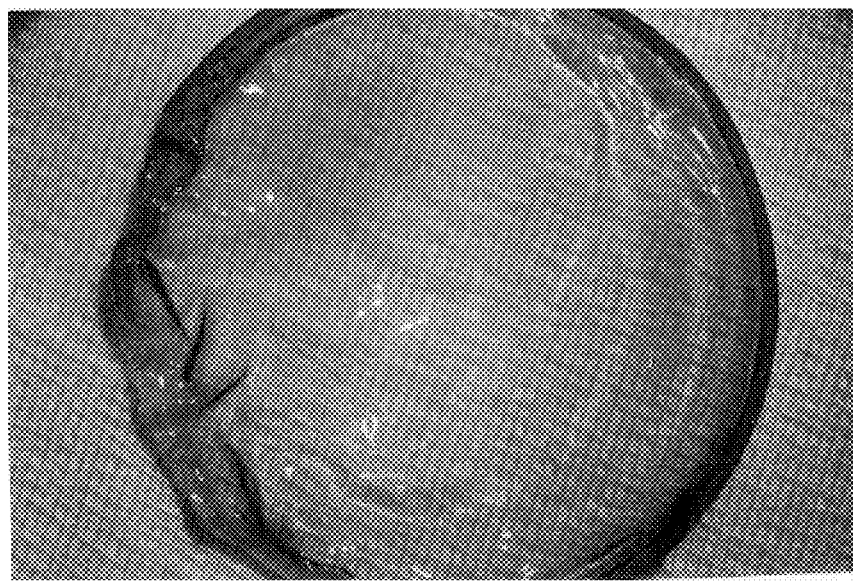
Figure 5A:
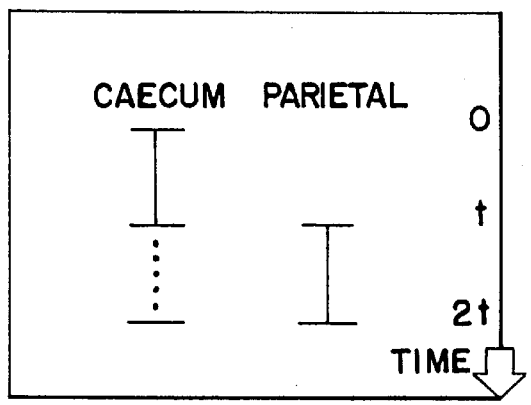
Figure 5B:
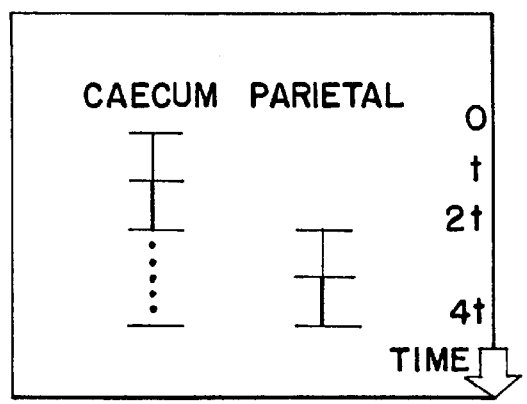
Figure 5C:
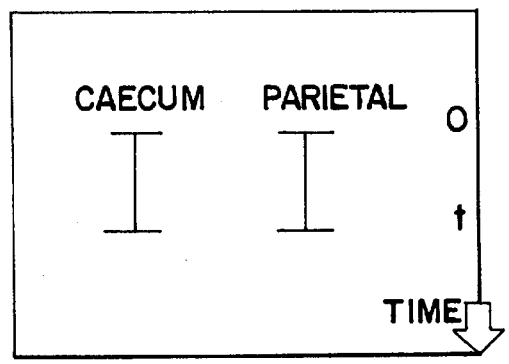
Figure 5D:
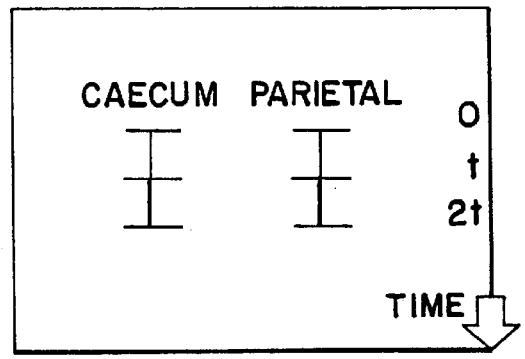

FIG. 4B Fibrin film in accordance with Example 2.

FIG. 5 Scheme showing the different types and modes of application using fibrin glues.

Figure 6:
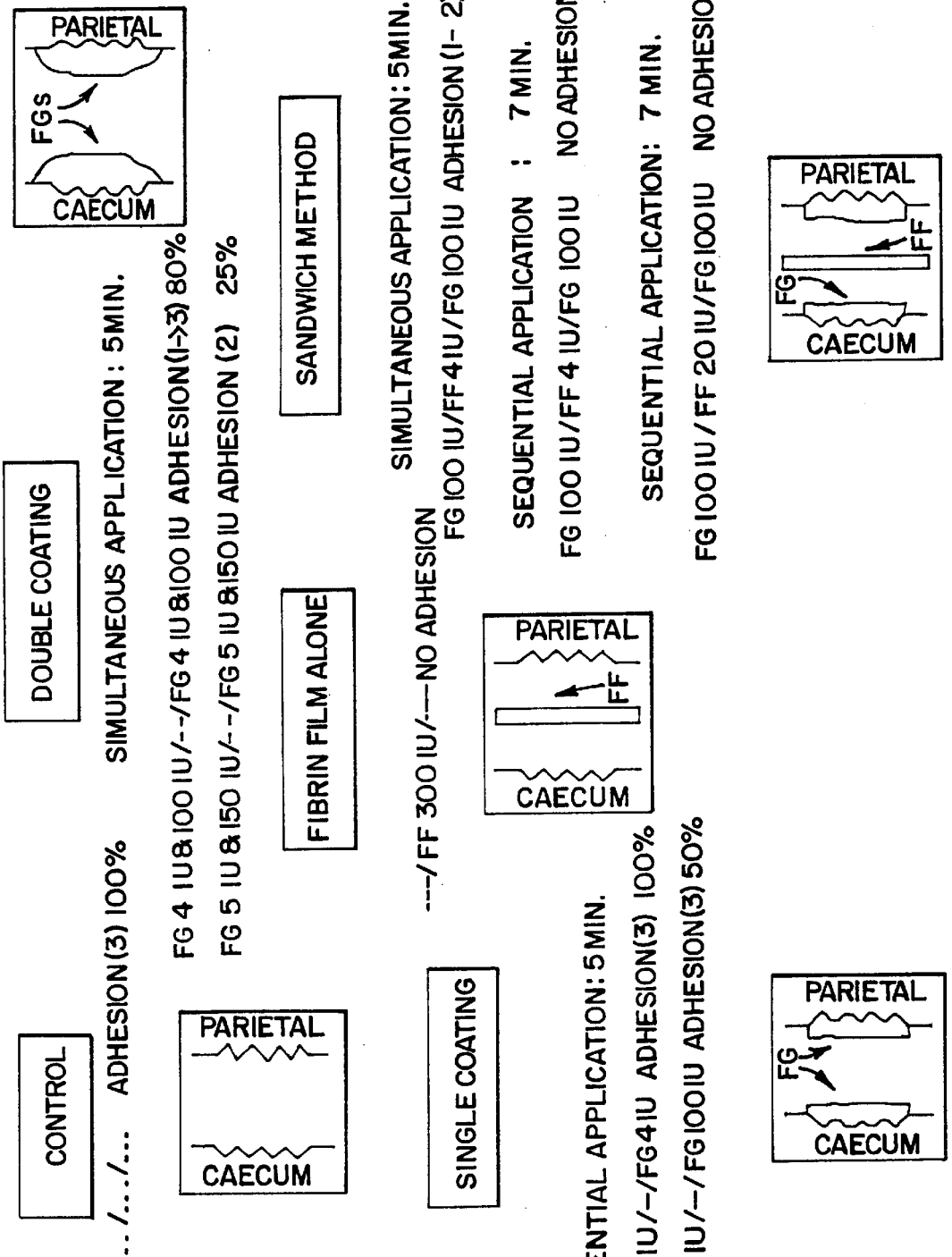

FIG. 6 Scheme summarizing the different embodiments of the invention according to the different experimental approaches.

FIGS. 7A–7E Technical drawing showing different views of the clamp having been used in the course of the animal model.

1. MATERIALS AND METHODS

1.1 Animals

For these studies, female Wistar rats weighing 180–200 g each were used. Before surgery the animals were kept in groups in cages and after surgery until necropsy they were kept alone. The strain designation is ICO.WI / (IOPS, CPB). The experiments were performed following the guidelines of the "*Législation et réglementation relative à l'expérimentation animale*".

1.2 Materials

For these experiments, Baxter Fibrin Sealants kits lot #26302001AA were used. While these kits are not on the market yet, in the light of the present disclosure any standard two-component fibrin sealant kit may be used for the purposes of the invention.

Calcium Chloride 20 mM from Nycomed lot #931343 Petri dish (9 cm diameter) from Nunc (cell culture quality)

1.3 Surgical and Anaesthetic Equipment

The surgical equipment included: PVC plate (surgery table) 30×30 cm; needle holders CRILE-WOOD, 14 cm; forceps; Wangesteen, 15 cm; standard anatomic forceps, 13 cm; dissecting scissors, Metzenbaum, 14 cm; home-made clamp (for fixing a tissue surface of 2 $cm^2$); lamp, Well-Lynch; scalpels SWANN-MORTON disposable #24; surgical suture USP Dermalon non-absorbable, Dermalon 2.0 needle CE4, Dermalon 4.0 needle CE-6; gauze swabs: layer 12, 10×10 cm Mölnlycke. Diethyl ether was used as anaesthetitice The home-made clamp shown in FIG. 7 serves as a tool to standardize the injuries inflicted on the surface of the parietal wall in terms of their position, area and depth. The clamp consists of two mobile parts. The 'male' part has rounded edges and embraces an area of 2 $cm^2$ corresponding to the surface of the smallest caecum found in a rat. When the clamp is closed, there is a gap of 2 mm between the male and the female part, which gap is sufficient to keep the respective tissue (muscle layer, skin) immobile without any shearing or cutting. The mechanical tension induced by the clamp is necessary to allow easy separation of the first muscle layer from the second one when the clamped surface is incised with a scalpel. The tension allows better control of the depth of incision.

1.4 Disinfection and Biological Waste

Surgery equipment was disinfected and washed with 15–20 g/l Mucocit-R (Merz) as per the technical data sheet. For all materials as well as the dead animal carcasses, usual measures for waste disposal were taken.

1.5 Animal Surgery

The surgical procedure as described below, using the above-described clamp, allows production of adhesions of the same type in control experiments with an incidence of 100 percent.

The skin was cut following a 4 cm line joining the xyphoid and urinary aperture for a rat weighing 180–200 g with a pair of Metzenbaum scissors.

The skin edges were lifted and carefully dissected from the muscle wall on each side of the linea alba.

The abdominal muscle was incised along the linea alba over the 4 cm line as described above.

The caecum was gently removed and laid on gauze swab avoiding, at any time, contact with the latex gloves and damage by instruments.

The caecum was abraded with gauze on its upper side until only punctuate bleeding appeared.

The caecum was returned to the peritoneal cavity if no treatment had to be performed. If a treatment was carried out, the product to be tested was applied on the caecum, which was then gently returned to the peritoneal cavity.

In the next step, the home-made clamp described above was used which had been designed to standardize the injury inflicted on the parietal wall in terms of area, position and depth, thus ensuring a test model, where adhesions are achieved with a constant incidence of 100 percent. The clamp was symmetrically introduced through the midline incision, placed and fastened on the parietal wall facing the caecum, thus defining a constant peritoneal surface of 2cm², where the injury was to be produced. Then the clamp was turned inside out to expose the parietal wall.

The exposed serosal surface was incised through the first muscular layer with 2×10 crossed incisions of constant depth.

After this step, the incised surface was replaced on the abraded caecum if no treatment had to be performed. If a treatment was performed, the product was applied on the incised surface and then carefully replaced on the abraded caecum such that caecum and parietal wall were separated by the product.

At that time, care was taken to avoid any movement that could induce distension or stretching, especially to the parietal caecum side.

The muscle was sutured with non-absorbable dermalon 2.0 and the skin closed with dermalon 4.0.

The animal identification was performed by using an electronic tag (ZETES Electronic Inc.) defined by an univocal key of 12 alpha-numeric digits.

Then the animals were allowed to recover in the laboratory.

1.6 Sham Control

A 'Sham' was performed by following all the steps of the surgical procedure, but without inflicting incisions or abrasions. Surgery timing was rigorously observed.

1.7 Animal Sacrifice

The animals were sacrificed after 10 days. The postmortem viscera studies were made through a U-shaped abdominal incision started at the liver level. Adhesions, present in the peritoneal cavity, were evaluated by two independent investigators.

1.8 Adhesion Classification

The adhesions were recorded according to their nature and tensile characteristics.

1.8.1 Nature of the Adhesion

The adhesions were classified in a table depending on the organs involved in the adhesion process. The adhesions involving the sutures were recorded, but will not be listed as adhesions hereinafter.

The main adhesion type observed and classified are:

caecum/parietal visceral/visceral fat/parietal fat/visceral fat/fat

The name of the fat or viscera in relationship with the "nature of the adhesion" will also be mentioned in parentheses.

e.g.: grade 2 adhesion between the fat of the uterus and the parietal wall will be reported as follows:

| fat / par |
|---|
| (Ut) (2) |

Ovary (O), Colon (Co), Ileum (Il), Bladder (Bl), and Omentum (Om) may also be involved in the adhesion process.

1.8.2 Tensile Characteristics

The adhesion was pealed off and evaluated according to the macromorphological adhesion grading scale (MAS) as follows:

0: no adhesion

1: filmy (mild)

7: adhesive bands (medium)

3: extensive adhesion formation (severe)

The adhesion tensile value was recorded in the appropriated column of the respective table with the type of organ involved in the adhesion process, as described above.

1.9 Type of Application

Two different types of application were performed with fibrin glue (FG): a "single coating" (one layer) or a "double coating" (two layeers).

1.9.1 Single Coating

A fibrin glue with a defined thrombin concentration was used as an haemostatic agent and tissue repair promoter, respectively.

Fibrin glue was applied as a "single coating" on the caecum and the parietal wall as described in paragraph 1.5.

1.9.2 Double Coating

Two fibrin glues, at two different concentrations of thrombin, a low and a high, were used.

The fibrin glue having the low thrombin concentration was used as a first layer of the double coating.

The fibrin glue having the high thrombin concentration, applied as "second layer", plays the role of mechanical barrier which entirely covers the injury and the first layer. The kinetic of fibrin formation of the second layer is faster than that of the first one and also the physical properties of the two layers are different.

1.10 Mode of Application

Caecum was abraded and the parietal wall was incised, respectively, and covered with a single or a double coating of fibrin glue (FG) depending on the protocol design.

Fibrin glue can be applied sequentially or simultaneously on both injured surfaces.

By combining the application type (single or double) and the application mode (sequential or simultaneous), four different cases can be obtained (cf. FIG. 5).

Case 1 single coating & sequential application

Case 2 double coating & sequential application

Case 3 single coating & simultaneous application

Case 4 double coating & simultaneous application (Case 2 will not be tested herein. Case 3 represents the "in vivo" conditions for the adhesion development.)

2. EXAMPLES

Example 1

Preparation of a Fibrin Film Using a Dual Syringe Device

The fibrin films were casted by using a commercial dual syringe device after reconstitution of the vials of a commercial fibrin glue kit in accordance with the information in the instruction leaflet of the respective kit employed. By way of example, a two-component fibrin glue kit comprising the following constituents may be used:

| Vial (1) | Human topical fibrinogen complex (dry concentrate) | |
|---|---|---|
| | protein | 10–13 g/100 ml |
| | clottable protein | 80% minimum |
| | albumin (human) | 0,5–1,5 g/100 ml |
| | plasminogen | 0,05 mg/ml maximum |
| | Factor XIII | 10–40 IU/ml |
| | polysorbate-80 | O,3 % (w/v) maximum |
| | pH | 7,1–7,5 |
| Vial (2) | Sterile water (3,5 ml) for reconstituting the content of vial (1) at 37° C. in a water bath | |
| Vial (3) | Human thrombin | |
| | potency | 300 ± 50 IU/ml |
| | albumin (human) | 0,05 ± 0,01 g/ml |
| | glycine | 0,30 M ± 0,05 M |
| | pH | 6,5–7,1 |
| Vial (4) | 35–45 mM CaCl₂ (3,5 ml) for reconstituting the content of vial (3) at room temperature | |

After reconstitution, the fibrinogen-containing solution was kept at room temperature. Further thrombin dilutions were made with 20 mM CaCl$_2$ as diluent. Using the dual syringe device, the mixture "Fibrinogen-Thrombin" was applied to a petri dish, while care was taken that at any time equal amounts of the fibrinogen-containing solution and the thrombin-containing solution were pressed out of the respective syringe. With low concentrations of thrombin, the petri dish was tilted to cover the surface with a fibrin glue of regular and homogenous thickness. With high concentrations of thrombin, particular care was taken that from the beginning the mixture of the fibrinogen-containing solution and the thrombin-containing solution was uniformly spread over the surface of the petri dish. The petri dish was incubated at 37° C. for two hours.

Optionally, disinfectants, e.g. methylene blue in a concentration of 10 mg/l–10 g/l or drugs, may be dissolved in the contents of vials (2) or (4) before these are used for reconstituting the contents of vials (1) and (2), respectively.

The fibrin film obtained may be air-dried and rehydrated before use. If the thrombin solution did not already comprise substances, like disinfectants or drugs for enhancing the desired therapeutic effect of the fibrin film, the solution used for rehydration may include those substances.

Example 2
Preparation of a Fibrin Film Using a Dry Fibrinogen Sheet

The solutions given in Example 1 were used with the following modifications.

3.5 ml of the reconstituted fibrinogen-containing solution were poured in a petri dish of 51 mm diameter which was tilted to spread the material all over the entire surface. The water contained in the fibrinogen-containing solution was evaporated by air drying. Thus, a dry fibrinogen sheet having a thickness of 100 μm and a weight of 0.4291 g was obtained. 3.5 ml of a reconstituted thrombin-containing solution were poured into the petri dish containing the dry, sheet-like fibrinogen material. The reaction mixture was then kept at 37° C. for 2 hours. The fibrin film thus obtained may either directly be used or be dried and rehydrated before use. Alternatively, the dry, sheet-like fibrinogen material may be converted into a fibrin film only before use.

Both the dry, sheet-like fibrinogen material and the dried fibrin film may be included in a commercial kit further comprising ancillary components for processing and rehydration, respectively, of the sheet-like materials.

Example 3
Preparation of a Fibrin Sealant/Glue

The preparation of a fibrin glue was performed as per the technical information of the instruction leaflet provided with the kit employed. The fibrin glue was prepared extemporaneously at different concentrations of thrombin, e.g. 4, 5, 20, 100, 150, and 300 IU/mi and used as described hereinbelow.

Example 4
"Control" Group

The animals were operated to develop adhesion, and therefore no treatment had been carried out. Accordingly, haemostasis was not achieved, and, thus, all conditions to develop with an incidence of 100% severe type 3 adhesions between the caecum and the parietal wall were present.

The results are reported in the following Table 1:

TABLE 1

Control Group

| No.* | Products applied | Adhesion | | | |
|---|---|---|---|---|---|
| | | Par. & Caec. | Visc. & Caec. | Fat & Caec. | Fat & Pariet. |
| 1 | ------ / - - - - - / ------ | (3) | (Ut)(1) | — | — |
| 2 | ------ / - - - - - / ------ | (3) | — | (Ut)(1) | (Om)(1) |
| 3 | ------ / - - - - - / ------ | (3)(xx) | — | — | — |
| 4 | ------ / - - - - - / ------ | (3) | — | (Ut)(1) | (Ut)(1) |
| 5 | ------ / - - - - - / ------ | (3)(xx) | — | — | — |
| 6 | ------ / - - - - - / ------ | (3)(xx) | — | — | — |
| 7 | ------ / - - - - - / ------ | (3) | — | — | — |
| 8 | ------ / - - - - - / ------ | (3)(xx) | — | — | — |
| 9 | ------ / - - - - - / ------ | (3) | — | — | — |
| 10 | ------ / - - - - - / ------ | (3) | — | — | (B1)(1) |
| 11 | ------ / - - - - - / ------ | (3) | — | — | — |
| 12 | ------ / - - - - - / ------ | (3) | — | — | (Om)(1) |
| 13 | ------ / - - - - - / ------ | (3) | — | — | — |
| 14 | ------ / - - - - - / ------ | (3) | — | (Om)(1) | (Om,Ut)(1, 1) |
| 15 | ------ / - - - - - / ------ | (3) | — | — | — |
| 16 | ------ / - - - - - / ------ | (3) | — | — | — |
| 17 | ------ / - - - - - / ------ | (3) | — | — | — |
| 18 | ------ / - - - - - / ------ | (3) | — | — | — |
| 19 | ------ / - - - - - / ------ | (3) | — | — | — |
| 20 | ------ / - - - - - / ------ | (3) | — | — | — |
| 21 | ------ / - - - - - / ------ | (3) | — | — | (Ut)(1) |

*Number of animal (female Wistar rat)
(x) = a piece of fibrin was still present

Example 5
Fibrin Film Application

As a rule the fibrin films used were made in accordance with Example 1.

Example 5a
Sham Control with Fibrin Film (FF)

Two animals were used as sham control. One received a fibrin film made using 3 IU thrombin and with water as diluent (FF 3 IU), the other received fibrin film made using 20 IU thrombin and with 20 mM CaCl$_2$ as diluent (FF 20 IU). No injuries were induced on the caecum and peritoneum.

No adhesions were observed with both animals. The results are reported in the following Table 2:

TABLE 2

Sham Control with Fibrin Film

| | | Adhesion | | | | | |
|---|---|---|---|---|---|---|---|
| No.* | Product applied | Par. & Caec. | Visc. & Caec. | Fat & Caec. | Fat & Pariet. | Fat & Visc. | Fat & Fat |
| 1 | SHAM(FF 20 IU) | — | — | — | — | — | — |
| 2 | SHAM(FF 3 IU) | — | — | — | — | — | — |

* = Number of animal (Female Wistar rat)

Example 5b
Application of a Fibrin Film without Control of Haemostasis

Fibrin films FF 3 IU and FF 20 IU in accordance with Example 5a were used as mechanical barrier without controlling haemostasis on the caecum and parietal injuries. Alternatively, a Fibrin Film 300 IU was used as mechanical barrier.

The animal sacrificed after 10 days showed medium caeco-parietal adhesions (type 2) and large number of fat adhesions, involving mainly uterus and bladder. Surprisingly and most importantly, the animals treated with FF 300 IU virtually did not develop any adhesions.

The results are reported in the following Table 3:

TABLE 3

Fibrin Film Alone

| | | Adhesion | | | | | |
|---|---|---|---|---|---|---|---|
| No.* | Product applied | Par. & Caec. | Visc. & Caec. | Fat & Caec. | Fat & Pariet. | Fat & Visc. | Fat & Fat |
| 1 | FF 3 IU | —o | —o | —o | —o | —o | —o |
| 2 | FF 3 IU | —o | —o | —o | —o | —o | —o |
| 3 | FF 3 IU | — | — | (Ut) (2) | (Ut, Bl) (3, 2) | — | — |
| 4 | FF 3 IU | (2) | — | (Om, Ut, Bl) (2, 2, 2) | (Om)(2) | — | — |
| 5 | FF 3 | (2) | — | (Ut) (2) | — | — | — |
| 6 | FF 3 | (1) | — | (Ut, Bl) (2,2) | (Ut)(2) | — | — |
| 7 | FF 20 IU | (2) | — | (Ut) (2) | (Ut)(2) | — | — |
| 8 | FF 20 IU | (3) | — | — | — | — | — |
| 9 | FF 20 IU | (3) | — | (Ut) (1) | — | — | — |
| 10 | FF 20 IU | (1) | — | — | — | — | — |
| 11 | FF 300 IU | — | — | — | — | — | — |
| 12 | FF 300 IU | — | — | (Ut) (L) | — | — | — |
| 13 | FF 300 IU | — | — | — | — | — | — |
| 14 | FF 300 IU | — | — | — | — | — | — |

* = Number of animal female Wistar rat)
o = Necropsy after 3 days/others after 10 days The fibrin film in accordance with the invention which was used for the treatment of animal no. 11 was obtained by an alternative process as follows:

The first, fibrinogen-containing solution was poured in a petri dish having a diameter of 91 mm. The temperature of said solution was decreased bating the petri dish for a few minutes at low temperature, here for 4 min at −12° C. Then the second, thrombin-containing solution (RT) was added and mixed with the first solution. The petri dish was incubated until completion of the conversion of fibrinogen to fibrin, here for 24 hours at 37° C.

Example 6
Fibrin Glue "Single Coating"

Using thrombin-containing solutions comprising 4 IU/mi (cf. Example 6a) and 100 &U/ml thrombin (cf. Example 6b), fibrin glues were applied as haemostatic agent to the abraded caecum and the incised peritoneum each. By way of Example, this is shown in the following Table as follows: FG 4 IU/ - - -/FG 4 IU; where (- - -) indicates that no fibrin film is placed between the injuries. The fibrin glue was applied to the injuries in sequence. The waiting time to allow a setting of the fibrin glue was 5 minutes after each application.

In Example 6a, severe type 3 adhesions between the caecum and the parietal wall were observed.

The results are shown in the following Table 4:

TABLE 4

Single Coating. Sequential Application Time: 5 min

| | | Adhesion | | | |
|---|---|---|---|---|---|
| No.* | Products applied | Par. & Caec. | Visc. & Caec. | Fat & Caec. | Fat & Pa-riet. |
| 1 | FG 4 IU / - - - - / FG 4 IU | (3) | — | — | — |
| 2 | FG 4 IU / - - - - / FG 4 IU | (3) | — | — | — |
| 3 | FG 4 IU / - - - - / FG 4 IU | (3) | — | — | — |
| 4 | FG 4 IU / - - - - / FG 4 IU | (3) | — | — | — |
| 5 | FG 4 IU / - - - - / FG 4 IU | (3) | — | — | — |

* =Number of animal (female Wistar rat)

In Example 6b, two animals developed severe type 3 adhesions between caecum and parietal wall. The caecum was partly included into the parietal wall. Two animals did not develop adhesion.

The results are reports in the following Table 5:

TABLE 5

Single Coating. Sequential Application Time: 5 min

| | | Adhesion | | | |
|---|---|---|---|---|---|
| No.* | Products applied | Par. & Caec. | Visc. & Caec. | Fat & Caec. | Fat & Pa-riet. |
| 1 | FG 100 IU / - - - - / FG 100 IU | (3) | — | (1, 1) | (Om, Ut) |
| 2 | FG 100 IU / - - - - / FG 100 IU | — | — | — | — |

TABLE 5-continued

Single Coating. Sequential Application Time: 5 min

|  | Products | | Adhesion | | |
|---|---|---|---|---|---|
| No.* | applied | Par. & Caec. | Visc. & Caec. | Fat & Caec. | Fat & Pa- riet. |
| 3 | FG 100 IU / - - - - / FG 100 IU | — | — | — | — |
| 4 | FG 100 IU / - - - - / FG 100 IU | (3) | — | — | — |

* = Number of animal (female Wistar rat

Example 7
Fibrin Glue "Double Coating"
Fibrin glues were applied at two different thrombin concentrations.

Example 7a

A first layer of a fibrin glue made using a thrombin-containing solution comprising 4 IU/ml thrombin (FG 4 IU) was simultaneously (i.e., only with a minimal delay caused by the handling) applied to both the abraded caecum and the incised parietal wall.

After a waiting time of 5 minutes to allow the polymerization, a second layer of fibrin glue 100 IU, FG 100 IU, was simultaneously applied on the same organs. This was followed by a second waiting time of 5 minutes before the surgical procedure was continued.

One animal did not develop adhesion. With one animal, which developed a severe type 3 adhesion, a remaining piece of fibrin was observed. Three animals developed mild type I adhesions between the caecum and the parietal wall.

The results are reported in the following Table 6:

TABLE 6

Double coating with FG 4 IU and FG 100 IU.
Simultaneous Application Time: 5 minutes

|  | Products | | Adhesion | | |
|---|---|---|---|---|---|
| No.* | applied | Par. & Caec. | Visc. & Caec. | Fat & Caec. | Fat & Pariet. |
| 1 | FG 4 & 100 IU / - - - / FG 4 & 100 IU | (3)(x) | — | (1, 1) | (Om, Ut) |
| 2 | FG 4 & 100 IU / - - - / FG 4 & 100 IU | (1) | — | — | — |
| 3 | FG 4 & 100 IU / - - - / FG 4 & 100 IU | (1) | — | — | — |
| 4 | FG 4 & 100 IU / - - - / FG 4 & 100 IU | — | — | — | — |
| 5 | FG 4 & 100 IU / - - - / FG 4 & 100 IU | (1) | — | — | — |

*= Number of animal (female Wistar rat)
(x) = a piece of fibrin was still present Example 7b A parallel experiment under the same conditions was conducted, but with the single exception that higher thrombin concentrations (FG 5 IU and FG 150 IU) were used.

Four animals did not develop adhesion. With one animal, which developed a mild type 2 adhesion between the caecum and the parietal wall, a remaining piece of fibrin was observed.

The results are reported in the following Table 7:

TABLE 7

Double coating with FG 5 IU and FG 150 IU
Simultaneous Application Time: 5 minutes

|  | Products | | Adhesion | | |
|---|---|---|---|---|---|
| No.* | applied | Par. & Caec. | Visc. & Caec. | Fat & Caec. | Fat & Pariet. |
| 1 | FG 5 & 150 IU / - - - / FG 5 & 150 IU | (2)(x) | — | — | — |
| 2 | FG 5 & 150 IU / - - -/ FG 5 & 150 IU | — | — | — | — |
| 3 | FG 5 & 150 IU / - - -/ FG 5 & 150 IU | — | — | — | — |
| 4 | FG 5 & 150 IU / - - -/ FG 5 & 150 IU | — | — | — | — |

*= Number of animal (female Wistar rat)
(x) = a piece of fibrin was still present Example 8

Sandwich Method—Use of a Combination of a Fibrin Glue and a Fibrin Film

The sandwich method combines the use of a fibrin glue as haemostatic agent/wound repair promoter and of a fibrin film as mechanical barrier. Three types of fibrin film which had been made using 4 IU, 20 IU and 300 IU thrombin in accordance with Example 1 were used. Due to the different thrombin concentrations of the respective fibrin films, the time required for complete fibrinogen-fibrin conversion varied. However, this is of no importance as the films were kept at 37° C. for more than two hours, a time greater than that required as determined theoretically and practically by means of turbidity measurement.

Example 8a

A fibrin glue 100 IU used as haemostatic agent was applied simultaneously both to the abraded caecum and the incised parietal wall with a waiting time of 5 minutes. In parallel (cf. (ii)), it was applied sequentially to the abraded caecum and the incised parietal wall with a waiting time of 7 minutes each time. In both experiments, a fibrin film of 4 IU was used.

(i) Simultaneous Application Time: 5 minutes

Two animals did not develop adhesions between caecum and parietal wall, while two animals developed mild type I adhesions between these surfaces. One animal developed a type 2 caeco-parietal adhesion.

The results are reported in the following Table 8:

TABLE 8

Sandwich Method. Simultaneous Application Time: 5 minutes

|  | Products | | Adhesion | | |
|---|---|---|---|---|---|
| No.* | applied | Par. & Caec. | Visc. & Caec. | Fat & Caec. | Fat & Pariet. |
| 1 | FG 100 IU / FF 4 IU / FG 100 IU | — | (Ut)(1) | — | — |
| 2 | FG 100 IU / FF 4 IU / FG 100 IU | (1) | — | — | — |
| 3 | FG 100 IU / FF 4 IU / FG 100 IU | (1) | — | — | — |

TABLE 8-continued

Sandwich Method. Simultaneous Application Time: 5 minutes

| No.* | Products applied | Adhesion | | | |
|---|---|---|---|---|---|
| | | Par. & Caec. | Visc. & Caec. | Fat & Caec. | Fat & Pariet. |
| 4 | FG 100 IU / FF 4 IU / FG 100 IU | — | — | — | — |
| 5 | FG 100 IU / FF 4 IU / | (2) | — | — | — |

*= Number of animal (female Wistar rat)

(ii) Sequential Application Time: 7 minutes

Virtually none of the animals developed adhesion.
The results are reported in the following Table 9:

TABLE 9

Sandwich Method. Sequential Application Time: 7 minutes

| No.* | Products applied | Adhesion | | | |
|---|---|---|---|---|---|
| | | Par. & Caec. | Visc. & Caec | Fat & Caec. | Fat & Pariet. |
| 1 | FG 100 IU / FF 4 IU / FG 100 IU | — | — | — | — |
| 2 | FG 100 IU / FF 4 IU / FG 100 IU | — | — | — | — |
| 3 | FG 100 IU / FF 4 IU / FG 100 IU | — | — | — | (B1)(1) |
| 4 | FG 100 IU / FF 4 IU / FG 100 IU | — | — | — | — |
| 5 | FG 100 IU / FF 4 IU / FG 100 IU | — | — | — | — |
| 6 | FG 100 IU / FF 4 IU / FG 100 IU | — | — | — | — |

*= Number of animal (female Wistar rat)

Example 8b

In another experiment, a fibrin glue 100 IU and a fibrin film 20 IU were used in combination. The fibrin glue was sequentially applied to the abraded caecum and to the incised parietal wall with a waiting time of 7 minutes each.

None of the animals developed adhesion.

The results are reported in the following Table 10:

TABLE 10

Sandwich Method. Sequential Application Time: 7 minutes

| No.* | Products applied | Adhesion | | | |
|---|---|---|---|---|---|
| | | Par. & Caec. | Visc. & Caec. | Fat & Caec. | Fat & Pariet. |
| 1 | FG 100 IU / FF 20 IU FG 100 IU | — | — | — | — |
| 2 | FG 100 IU / FF 20 IU FG 100 IU | — | — | — | — |
| 3 | FG 100 IU / FF 20 IU / FG 100 IU | — | — | — | — |

*= Number of animal (female Wistar rat)

Example 8c

In a further experiment, a fibrin glue 100 IU was combined with a fibrin film 300 IU. The fibrin film of the invention was obtained in accordance with the alternative method mentioned in Example 5 (cf. animal no. 11), but with an incubation of 10 min. at −12° C. The fibrin film thus obtained was air dried and then rehydrated before being used like a fibrin film made in accordance with Examples 1 and 2. As in Example 8b, the fibrin glue was sequentially applied to the abraded caecum and the incised parietal wall with an application time of 7 minutes each.

One animal developed a very mild adhesion. The other four animals did not develop any adhesions.

The results are summarized in the following Table 11:

TABLE 11

Sandwich Method. Sequential Application Time: 7 minutes

| No.* | Products applied | Adhesion | | | |
|---|---|---|---|---|---|
| | | Par. & Caec. | Visc. & Caec. | Fat & Caec. | Fat & Pariet. |
| 1 | FG 100 IU / FF 300 IU (*) / FG 100 IU | (<1) | — | — | — |
| 2 | FG 100 IU / FF 300 IU (*) / FG 100 IU | — | — | — | — |
| 3 | FG 100 IU / FF 300 IU (*) / FG 100 IU | — | — | — | — |
| 4 | FG 100 IU / FF 300 IU (*) / FG 100 IU | — | — | — | — |
| 5 | FG 100 IU / FF 300 IU (*) / FG 100 IU | — | — | — | — |

*= Number of animal (female Wistar rot)
(*) = prepared at −12 ° C. for 10 minutes

Example 8d

In addition, experiments were performed using a fibrin film FG 20 IU in combination with fibrin films of 20 IU and 300 IU, respectively. The fibrin films were made in accordance with Example 1, air-dried and then rehydrated before use. As in Example 8c, the fibrin glue was sequentially applied to the abraded caecum and the incised parietal wall with a waiting time/application time of 7 minutes each.

None of the animals developed any adhesions.

The results are summarized in the following Table 12:

TABLE 12

Sandwich Method. Sequential Application Time: 7 minutes

| No.* | Products applied | Adhesion | | | |
|---|---|---|---|---|---|
| | | Par. & Caec. | Visc. & Caec. | Fat & Caec. | Fat & Pariet. |
| 1 | FG 20 IU / FF 20 IU / FG 20 IU | — | — | — | — |
| 2 | FG 20 IU / FF 20 IU / FG 20 IU | — | — | — | — |
| 3 | FG 20 IU / FF 300 IU / FG 20 IU | — | — | — | — |
| 4 | FG 20 IU / FF 300 IU / FG 20 IU | — | — | — | — |

*= Number of animal (female Wistar rat)

3. DISCUSSION 3.1 Application of a Fibrin Film without Control of Haemostasis

As shown in Example 5b, fibrin films made by using 3 IU and 20 IU, if used in an uncontrolled haemostatic environment, did not prevent adhesion formation. On the other hand, the use of fibrin films with high thrombin concentration completely prevented adhesion formation without haemostatis being performed.

32 Single Coating

Sequential application of FG 4 IU (cf. Example 6a) did not prevent adhesion formation at all, whereas sequential application of FG 100 IU (cf. Example 6b) allowed a 50% prevention of adhesion formation. These findings suggest that the conversion of fibrinogen to fibrin was not complete on both caecum and parietal wall.

3.3 Double Coating

The simultaneous application of FG 4 & 100 for five minutes was still too short to prevent adhesion formation, but decreased the adhesion grade and tensile properties (cf. Example 7a).

In Example 7b, rather than to increase the simultaneous application time/waiting time for achieving complete fibrinogen-fibrin conversion, the thrombin concentrations were increased in order to reduce the clotting time. In fact, with the simultaneous application of FG 5 & 150 for five minutes, the number of adhesions was decreased.

The presence of a remaining fibrin piece in Examples 7a and 7b indicates, however, that the application volume had to be better controlled. It also has to be pointed out that the double coating of fibrin glues was applied to an injured area where the fibrinolytic system was dramatically impaired. A more controlled delivery (by better handling) and a lower volume of fibrin glue at a higher thrombin concentration (to achieve a faster and more complete conversion of fibrinogen to fibrin) seem to be more suitable for improving the outcome.

3.4 Sandwich Method Using a Fibrin Glue and a Fibrin Film

As shown in Table 8, simultaneous application of FG 100 IU/FF 4 IU/FG 100 IU for five minutes did not totally prevent adhesion formation. The fibrin film made by using 4 IU thrombin is indeed a stabilized film having a complete fibrinogen-fibrin conversion, but the inventors are aware that such a fibrin film has particularly large and opened pores. On the other hand, Table 8 shows that FG 100 IU, applied with a waiting time of five minutes, did not completely prevent the development of adhesions. Thus, it may be that FG 100 IU had not reached completion of the conversion of fibrinogen to fibrin and interacted with FF 4 IU in such a manner that no complete prevention of adhesion formation was achieved.

Principally, this could be avoided by either increasing the thrombin concentration of the fibrin glue used (to achieve a faster clotting) or by increasing its sequential application time (to provide more time for the fibrinogen-fibrin conversion), or by increasing the thrombin concentration of the fibrin film (to produce smaller pores).

As shown in Table 9, when increasing the sequential application time up to seven minutes, the application of FG 100 IU/FF 4 IU/FG 100 IU prevented adhesion formation. Likewise, adhesion formation was prevented by increasing the thrombin concentration of the fibrin film to 20 IU as can be taken from Table 10.

It appeared interesting to test a fibrin film made by using a very high thrombin concentration (300 IU). In this case (cf. Table 11), the first coating to control haemostasis (FG 100 IU) as well as application mode and time were maintained in order to compare this situation with the previous examples. In the light of the present disclosure (cf. Table 12), those of skill in the art will appreciate that different combinations may lead to excellent results in the prevention of adhesion formation. Finally, it is pointed out that interestingly the fibrin film FF 300 IU completely prevented adhesion formation without haemostasis having been performed, while this was not achieved by using FF 20 IU. The above-described experiments indicate that with the sandwich technique even fibrin films having a pore size above 5 µm may be used, while the fibrin films preferably should have a pore size below 5 µm when used alone, i.e., without control of haemostasis.

We claim:

1. A method of using a self-supporting film material of cross-linked fibrin for the preparation of a medicament for the prevention of adhesion formation as a post-operative complication, comprising the step of applying the film material of cross-linked fibrin to an injured surface, wherein the film material of cross-linked fibrin is prepared by the steps comprising:

(a) converting fibrinogen to fibrin using a thrombin-containing solution having a concentration of at least 20 IU/ml;

(b) converting the fibrinogen such that the conversion to fibrin is substantially complete in that there is essentially no unreacted fibrinogen in the fibrin material; and (c) forming a fibrin material having a pore size of below 5 µm.

2. The method of claim 1, wherein the cross-linked fibrin material is non-haemostatic.

3. The method of claim 1, further comprising the step of separating the injured surface from another surface.

4. The method of claim 1, wherein the fibrin material is used in combination with a fibrin glue.

5. The method of claim 4, wherein the fibrin glue is used for the treatment of the injured surface.

6. The method of claim 5, wherein the fibrin glue applied to the injured surface has been made by mixing a fibrinogen-containing solution having a factor XIII content of 10–40 IU/ml with an equal volume of a thrombin-containing solution comprising 1–300 IU/ml thrombin, and calcium; said fibrinogen-containing solution being a protein solution with a content of 90–140 mg protein/ml comprising up to 90% clottable protein.

7. The method of claim 5, wherein the fibrin glue is allowed to set undisturbed on the surface applied to until the conversion of fibrinogen to fibrin is complete.

8. The method of claim 1, wherein said fibrin material has a regular pore size.

9. The method of claim 1, wherein the fibrin material in the wet state has a thickness of at least 20 µm.

10. The method of claim 1, wherein the fibrin material further comprises at least one additive selected from the group consisting of antibiotics, fibrinolytic agents and biological response modifiers.

11. A process of preparing a self-supporting film material of cross-linked fibrin, said process comprising the steps of:

a. simultaneously mixing a stream of a first, fibrinogen-containing solution with a stream of a second, thrombin-containing solution having a concentration of at least 20 IU/ml;

b. applying the obtained mixture to a solid support;

c. incubating the mixture until the conversion of fibrinogen to fibrin is substantially complete such that there is essentially no unreacted fibrinogen in the fibrin material; and d. forming a fibrin material having a pore size of below 5 µm.

12. The process of claim 11, wherein in step (a) equal volumes of the first and second solution are mixed.

13. The process of claim 11, wherein the mixing in step (a) is performed using a dual syringe device.

14. The process of claim 11, wherein the first, fibrinogen-containing solution has a factor XIII content of 10–40 IU/ml, and the second, thrombin-containing solution has a thrombin content of 20–300 IU/ml, and a calcium content of up to 45 mM, said first fibrinogen-containing solution being a protein solution with a content of 90–140 mg protein/ml comprising up to 90% clottable protein.

15. The process of claim 11, wherein at least one additive selected from the group consisting of antibiotics, fibrinolytic agents and biological response modifiers is added to the second, thrombin-containing solution.

16. The process of claim 11 wherein an autologous first solution is used.

17. The process of claim 11, wherein step (c) is performed at 37° C. for 1–200 min.

18. A process of preparing a self-supporting film material of cross-linked fibrin, said process comprising the steps of:
a. applying a first, aqueous, fibrinogen-containing solution having a factor XIII content of 10–40 IU/ml and a protein content of 90–140 mg protein/ml comprising up to 90% clottable protein to a solid support;

b. removing water until dryness, forming a sheet-like fibrinogen material;

c. applying to the sheet-like fibrinogen material a second, thrombin-containing solution having a thrombin content of 20–300 IU/ml and a calcium content of up to 45 ml; and d. incubating until the conversion of fibrinogen to fibrin is substantially complete such that there is essentially no unreacted fibrinogen in the fibrin material to form said fibrin material having a pore size of below 5 $\mu$m.

19. The process of claim 18, wherein in steps (a) and (c) equal volumes of the first and the second solutions are used.

20. The process of claim 18 wherein in step (b) water removal is performed by a process selected from the group consisting of air-drying, freeze-drying, and drying under increased temperature and reduced pressure.

21. The process of claim 18, wherein step (d) comprises incubating at 37° C. for about 20 min. to about 200 min.

22. The process of using a first fibrin glue acting as a haemostatic agent in combination with a second fibrin glue acting as a bio-mechanical barrier for the preparation of a medicament for the prevention of adhesion formation as a post-operative complication, wherein the second fibrin glue is prepared by the steps comprising:

(a) converting fibrinogen to fibrin using a thrombin-containing solution having a concentration of at least 20 IU/ml;

(b) converting the fibrinogen such that the conversion to fibrin is substantially complete in that there is essentially no unreacted fibrinogen in the fibrin material; and (c) forming a fibrin material having a pore size of below 5 $\mu$m.

23. The process of claim 22, wherein the first and second fibrin glues are applied to a lesion in sequence.

24. The process of claim 22, further comprising the steps of applying the first fibrin glue to the lesion, allowing the first fibrin glue to set, and applying the second fibrin glue.

25. The process of claim 22 wherein the first fibrin glue has been made by mixing a fibrinogen-containing solution having a factor XIII content of 10–40 IU/ml and a protein content of 90–140 mg protein/ml comprising up to 90% clottable protein with an equal volume of a thrombin-containing solution comprising less than 1000 IU/ml thrombin and the second fibrin glue has been made by mixing said fibrinogen-containing solution with an equal volume of a thrombin-containing solution comprising at least 50 IU/ml thrombin and calcium.

26. The process of claim 22 wherein a double coating is obtained.

27. The method of claim 1, further comprising the step of isolating an injured surface from another surface.

28. The method of claim 1 comprising the further step of forming a fibrin material having a pore size of below 1 $\mu$m.

29. The method of claim 1 wherein the fibrin material in a wet state has a thickness of 20–2000 $\mu$m.

30. The method of claim 1 wherein the fibrin material in a wet state has a thickness of 5000 $\mu$m.

31. The method of claim 4 wherein the fibrin glue is used for haemostatis.

32. The method of claim 6 wherein the thrombin-containing solution comprises at least 20 IU/ml thrombin.

33. The method of claim 6 wherein the thrombin-containing solution comprises at least 100 IU/ml thrombin.

34. The method of claim 10 wherein the biological response modifier is selected from the group consisting of cytokines and wound repair promoters.

35. The process of claim 11 wherein the mixing step (a) is performed using a spray device.

36. The process of claim 11 wherein an autologous second solution is used.

37. The process of claim 11 wherein an autologous first and second solution are used.

38. The process of claim 11 wherein the fibrin material has a pore size of below 1 $\mu$m.

39. The process of claim 14 wherein the thrombin-containing solution comprises a thrombin content of more than 300 IU/ml thrombin.

40. The process of claim 15 wherein the biological response modifier is selected from the group consisting of cytokines and wound repair promoters.

41. The process of claim 18 wherein the fibrin material has a pore size of below 1 $\mu$m.

42. The process of claim 18 wherein the first fibrogen solution is autologous.

43. The process of claim 18 wherein the second thrombin-containing solution further comprises disinfectants or drugs selected from the group consisting of antibiotics, fibrinolytic agents and biological response modifiers.

44. The process of claim 43 wherein the biological response modifiers are selected from the group consisting of cytokines and wound repair promoters.

45. The process of claim 18 wherein the second thrombin-containing solution is autologous.

46. The process of claim 18 wherein an autologous first and second solution are used.

47. The process of claim 18 wherein the second thrombin containing solution has a thrombin content of more than 300 IU/ml thrombin.

48. The process of claim 21 wherein step (d) further comprises incubation at 37° C. for about 120 minutes.

49. The process of claim 25 wherein the thrombin-containing solution of the first fibrin glue comprises less that 150 IU/ml thrombin.

50. The process of claim 25 wherein the second fibrin glue comprises a thrombin-containing solution comprising at least 150 IU/ml thrombin.

51. The process of claim 25 wherein the second fibrin glue comprises a thrombin-containing solution comprising at least 300 IU/ml thrombin.

52. The process of claim 25 wherein the fibrinogen-containing solution is autologous.

53. The process of claim 25 wherein the thrombin-containing solution is autologous.

54. The process of claim 25 wherein the fibrinogen-containing solution and the thrombin-containing solution are autologous.

* * * * *